United States Patent
Giasson et al.

(10) Patent No.: US 11,434,281 B2
(45) Date of Patent: Sep. 6, 2022

(54) MONOCLONAL ANTIBODIES TARGETING PHF1 AND AT8 EPITOPES OF HUMAN TAU PROTEIN

(71) Applicant: University of Florida Research Foundation, Inc., Gainesville, FL (US)

(72) Inventors: Benoit Giasson, Gainesville, FL (US); Todd Eliot Golde, Gainesville, FL (US); Yona Levites, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 46 days.

(21) Appl. No.: 16/899,307

(22) Filed: Jun. 11, 2020

(65) Prior Publication Data

US 2020/0299370 A1 Sep. 24, 2020

Related U.S. Application Data

(63) Continuation-in-part of application No. PCT/US2018/065811, filed on Dec. 14, 2018.

(60) Provisional application No. 62/598,565, filed on Dec. 14, 2017.

(51) Int. Cl.
| | |
|---|---|
| *C07K 16/18* | (2006.01) |
| *A61K 49/00* | (2006.01) |
| *A61K 51/00* | (2006.01) |

(52) U.S. Cl.
CPC ........... *C07K 16/18* (2013.01); *A61K 49/001* (2013.01); *A61K 51/00* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2002/0188106 A1 | 12/2002 | Mandelkow et al. | |
| 2006/0008853 A1 | 1/2006 | Mercken et al. | |
| 2014/0377781 A1* | 12/2014 | Yoshida | C07K 16/30 435/7.23 |
| 2015/0196663 A1* | 7/2015 | Shusta | A61K 9/0085 424/178.1 |
| 2015/0266947 A1* | 9/2015 | Sierks | G01N 33/6896 424/135.1 |
| 2017/0355756 A1* | 12/2017 | Julien | A61P 21/02 |
| 2021/0349096 A1* | 11/2021 | Zhang | G01N 21/6428 |

FOREIGN PATENT DOCUMENTS

WO WO2008068048 * 6/2008

OTHER PUBLICATIONS

Kussie "A Single Engineered Amino Acid Substitution Changes Antibody Fine Specificity" J immunol 152(1):146-52 (Year: 1994).*
Strang et al., Generation and characterization of new monclonal antibodies targeting the PHF1 and AT8 epitopes on huam tau, Acta Neuropathologica Communications, vol. 5, No. 58, p. 1-11, 2017.
International Search Report issued for PCT/US2018/065881, dated Apr. 22, 2019.
Bi et al., Tau-targeted immunization impedes progression of neurofibrillary histopathology in aged P301L tau transgenic mice. PloS One 2011;6: e26860. Doi 10.1371/journal.pone.0026860.
Boutajangout et al., Passive immunization targeting pathological phospho-tau protein in a mouse model reduces functional decline and clears tau aggregates from the brain. J. Neurochem. 2011;118: 658-667. Doi 10.1111/i.1471-4159.2011.07337.x.
Goedert et al., Monoclonal antibody AT8 recognises tau protein phosphorylated at both serine 202 and threonine 205. Neurosci. Lett. 1995;189: 167-169.
Gu et al., Two novel Tau antibodies targeting the 396/404 region are primarily taken up by neurons and reduce Tau protein pathology. J. Biol. Chem. 2013;288: 33081-33095. Doi 10.1074/jbc.M113. 494922.
Hanger et al., New phosphorylation sites identified in hyperphosphorylated tau (paired helical filament-tau) from Alzheimer's disease brain using nanoelectrospray mass spectrometry. J. Neurochem. 1998;71: 2465-2476.
Hanger et al., Novel phosphorylation sites in tau from Alzheimer brain support a role for casein kinase 1 in disease pathogenesis. J. Biol. Chem. 2007;282: 23645-23654. Doi 10.1074/jbc. M703269200.
Ittner et al., Tau-targeting passive immunization modulates aspects of pathology in tau transgenic mice. J. Neurochem. 2015;132: 135-145. Doi 10.1111/jnc.12821.
Malia et al., Sweet RWet al. Epitope mapping and structural basis for the recognition of phosphorylated tau by the anti-tau antibody AT8. Proteins 2016;84: 427-434. Doi 10.1002/prot.24988.
Morishima-Kawashima et al., Proline-directed and non-proline-directed phosphorylation of PHF-tau. J. Biol. Chem. 1995;270: 823-829.
Mondragon-Rodriguez et al., Phosphorylation of tau protein at sites Ser(396-404) is one of the earliest events in Alzheimer's disease and Down syndrome. Neuropathol. Appl. Neurobiol. 2014;40: 121-135. Doi 10.1111/nan.12084.
Otvos et al., Monoclonal antibody PHF-1 recognizes tau protein phosphorylated at serine residues 396 and 404. J. Neurosci. Res. 1994;39: 669-673.

(Continued)

*Primary Examiner* — Adam Weidner
(74) *Attorney, Agent, or Firm* — Thomas | Horstemeyer, LLP

(57) ABSTRACT

Disclosed herein are monoclonal antibodies targeting specific tau epitopes, particularly, phosphorylated tau epitopes. Also disclosed are methods of detecting tau protein in a subject, comprising performing an assay using the antibodies or antigen binding fragments thereof on the subject or on a biological sample obtained from the subject. Assay kits containing the disclosed antibodies are also provided. Further, methods of treating or preventing a tauopathy in a subject by administering to the subject tau antibodies or antigen-binding fragments thereof are provided.

16 Claims, 17 Drawing Sheets

Specification includes a Sequence Listing.

(56) References Cited

OTHER PUBLICATIONS

Porzig et al., Epitope mapping of mAbs AT8 and Tau5 directed against hyperphosphorylated regions of the human tau protein. Biochem. Biophy. Res. Commun. 2007;358: 644-649. Doi 10.1016/j.bbrc.2007.04.187.

Walls et al., Tau immunotherapy reduces soluble and insoluble tau in aged 3xTg-AD mice. Neurosci. Lett. 2014;575: 96-100. Doi 10.1016/j.neulet.2014.05.047.

* cited by examiner

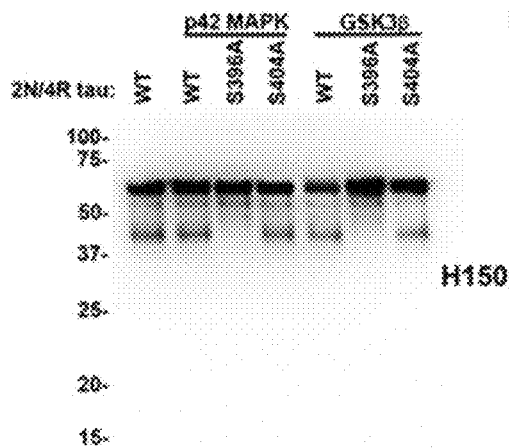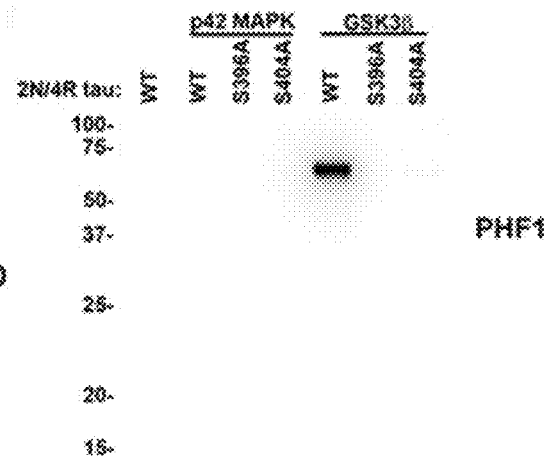
FIG. 1A    FIG. 1B
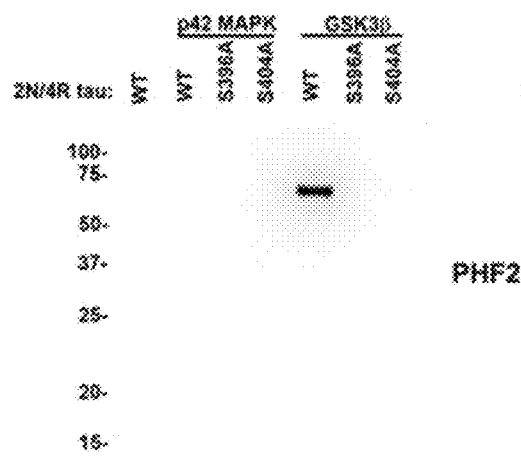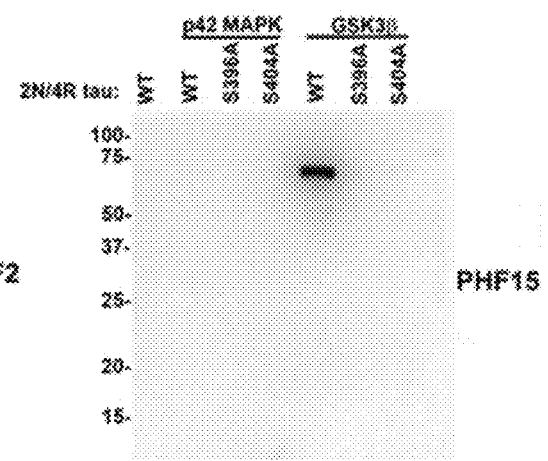
FIG. 1C    FIG. 1D

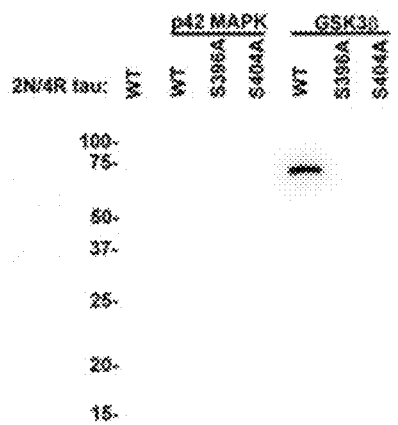
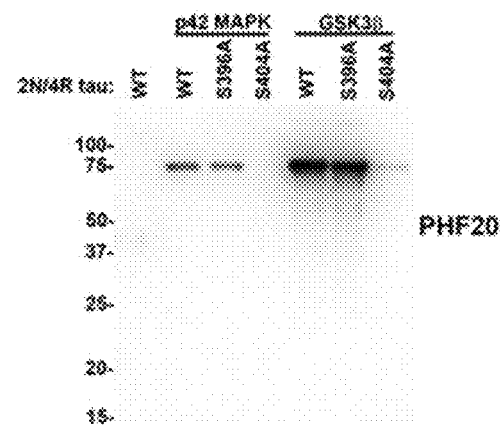
FIG. 1E    FIG. 1F
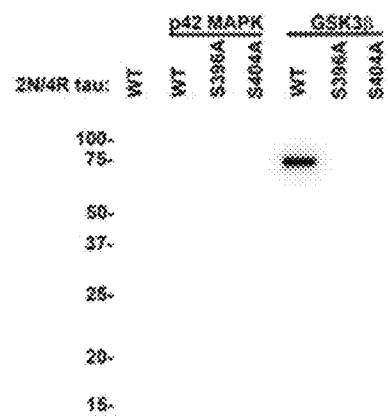
FIG. 1G

MONOCLONAL ANTIBODIES TARGETING PHF1 AND AT8 EPITOPES OF HUMAN TAU PROTEIN

CROSS-REFERENCE TO RELATED APPLICATIONS

This application is a continuation-in-part of co-pending Application Serial No. PCT/US2018/065811, filed Dec. 14, 2018, which claims benefit of U.S. Provisional Application No. 62/598,565, filed Dec. 14, 2017, which is hereby incorporated herein by reference in its entirety.

STATEMENT REGARDING FEDERALLY SPONSORED RESEARCH OR DEVELOPMENT

This invention was made with government support under Grant Nos. NS089622 and AG047266 awarded by the National Institutes of Health. The government has certain rights in the invention.

SEQUENCE LISTING

This application contains a sequence listing filed in electronic form as a 33 KB ASCII.txt file entitled "222110-2620 Sequence Listing.txt" created on Dec. 14, 2018. The content of the sequence listing is incorporated herein in its entirety.

BACKGROUND

Tau refers to the microtubule-associated protein expressed from the MAPT gene located on chromosome 17q21-22. In the adult human brain, six major tau isoforms ranging between 352 and 441 amino acids in length are produced as a result of alternative RNA splicing. Although tau is natively highly soluble, it can polymerize to form amyloid fibrils that aberrantly coalesce to form intracellular inclusions that define a large spectrum of neurodegenerative diseases termed tauopathies.

Alzheimer's disease (AD) is a common form of tauopathy where tau aggregates to form somatodendritic neurofibrillary tangles (NFTs), parenchymal neuropil threads and dystrophic neurites that are intertwined with extracellular deposits of amyloid-□ peptides. The abundance of tau inclusions in the brain correlates well with disease severity. However, the presence of tau pathological inclusions are also a defining feature of many other types of dementias, such as corticobasal degeneration, progressive supranuclear palsy, tangle-only dementia, Pick's disease, and frontotemporal dementia and parkinsonism linked to chromosome 17 with tau pathology (FTDP-17t). Indeed, FTDP-17t is caused by more than 50 different mutations in the MAPT gene, resulting in either tau protein amino acid changes or altered ratio of tau splicing isoforms, which suggests a pathogenic role of tau in neurodegeneration.

Hyperphosphorylation of tau is a hallmark of tau pathological inclusions in human brain and pathological findings indicate that phosphorylation of tau at specific residues, such as the in epitopes specifically recognized by antibodies AT8 and PHF1, occurs early in tau inclusion formation. Given the interest for these epitopes as pathological markers and for immunotherapy, monoclonal antibodies targeting these regions of tau with unique phosphorylation specificities are needed.

SUMMARY

Monoclonal antibodies that specifically recognize certain tau epitopes, particularly, phosphorylated tau epitopes are provided. Accordingly, certain embodiments of the disclosure provide antibodies or antigen binding fragments thereof that specifically recognize epitopes of tau that are also recognized by AT8 and PHF1 antibodies. In particular embodiments, the antibodies or antigen binding fragments thereof recognize epitopes of tau consisting of the amino acid sequence of SEQ ID NO: 3 or 4. Certain other antibodies or antigen binding fragments thereof recognize epitopes of tau consisting of the amino acid sequence of SEQ ID NO: 3 or 4, and having unique phosphorylation patterns.

The antibodies or antigen binding fragments thereof of the current disclosure can be monoclonal antibodies, such as murine monoclonal antibodies, human monoclonal antibodies, chimeric antibodies, human antibodies, humanized antibodies, intrabodies, single chain antibodies, single chain fragment variable (scFv) antibodies, or fragment antigen-binding (Fab fragment).

The current disclosure also provides methods of detecting tau protein in an animal, the method comprising performing an assay using the antibodies or antigen binding fragments thereof described herein on a subject or on a biological sample obtained from the subject. The assay can be an ELISA, for example, sandwich ELISA or competitive ELISA.

The current disclosure also provides kits, for example ELISA kits, comprising the antibody or antigen binding fragment thereof of the current disclosure. The antibodies or antigen binding fragments thereof can be labeled with an enzyme in the ELISA kits of the current disclosure. Alternately, the antibodies or antigen binding fragments thereof can be coated on to immunoassay plates.

Further embodiments of the disclosure provide methods of treating or preventing tauopathies in a subject by administering to the subject one or more tau antibodies or antigen-binding fragments thereof as disclosed herein. The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1F to 1G show specificity of tau antibodies raised against tau peptide p391-409 (SEQ ID NO: 3) as determined by immunoblotting with recombinant tau proteins phosphorylated in vitro with p42 MAPK or GSK3β. WT, S396A and S404A 2N/4R tau were incubated with p42 MAPK or GSK3 β or without any kinase as described in "Material and Methods". The proteins were resolved onto 10% polyacrylamide gels and analyzed by immunoblotting with the disclosed tau antibodies, namely, PHF2 (FIG. 1C), PHF15 (FIG. 1D), PHF17 (FIG. 1E), PHF20 (FIG. 1F), or PHF22 (FIG. 1G). Similar blots were performed with previously characterized antibody PHF1 (FIG. 1B) and total tau antibody H150 (FIG. 1A). The mobilities of molecular mass markers are shown on the left.

Figures 2A, 2B, 2C, 2D, 2E:
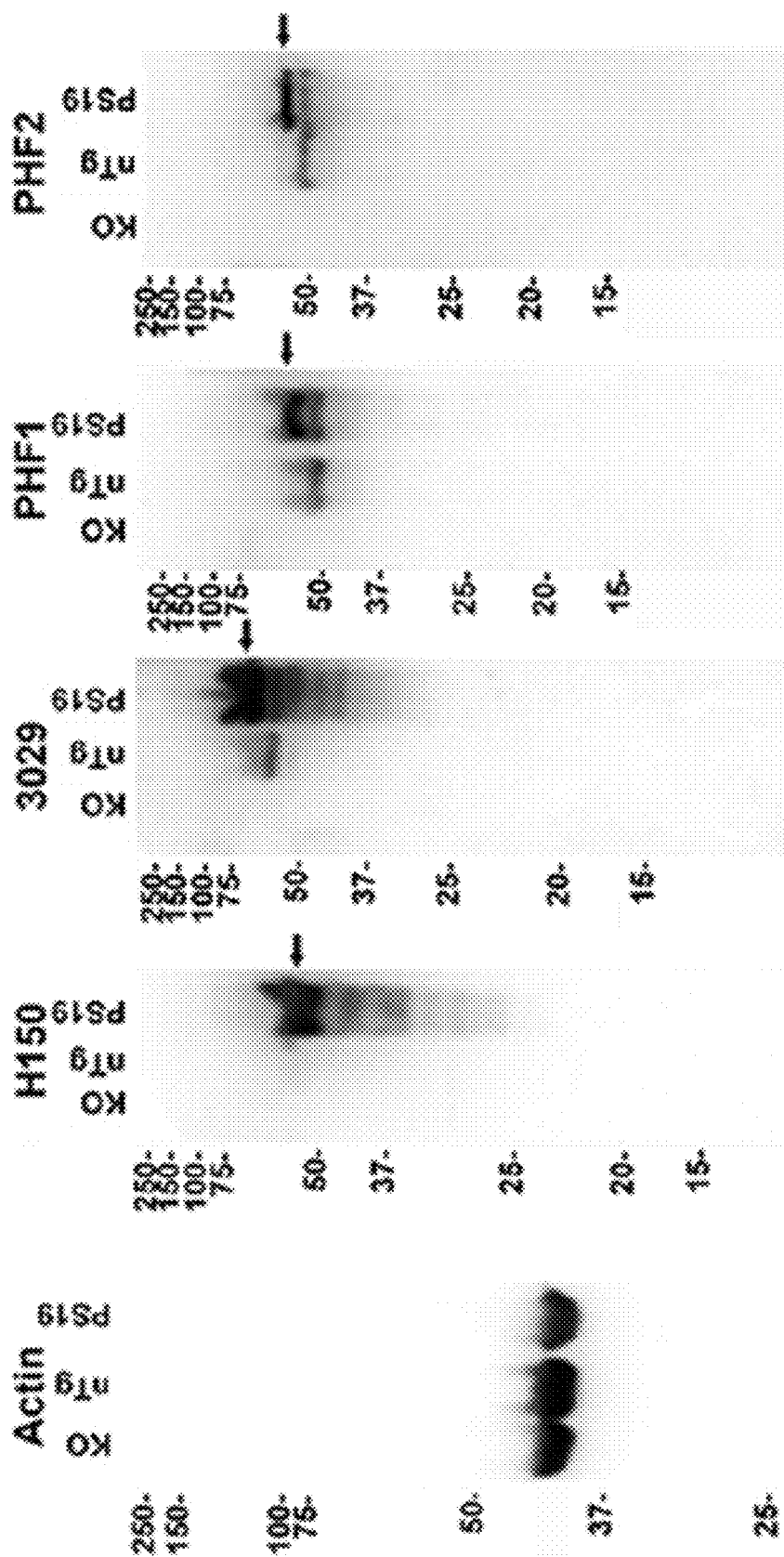
FIGS. 2A to 2S show characterization of the specificity of tau antibodies H150 (FIG. 2B), 3029 (FIG. 2C), PHF1 (FIG. 2D), PHF2 (FIG. 2E), PHF15 (FIG. 2F), PHF17 (FIG. 2G), PHF20 (FIG. 2H), PHF22 (FIG. 2I), AT8 (FIG. 2J), 1H5 (FIG. 2K), 2D1 (FIG. 2L), 3C9 (FIG. 2M), 4A10 (FIG. 2N), 5F2 (FIG. 2O), 6G12 (FIG. 2P), 7F2 (FIG. 2Q), 8G5 (FIG. 2R), 10G2 (FIG. 2S) by immunoblotting analyses using total brain lysates from nTg, tau KO and PS19 tau Tg mice, using actin as a control (FIG. 2A). Brains from tau KO, nTg, and PS19 tau Tg mice were harvested and lysed in 2% SDS/50 mM Tris pH 7.5 as described in "Material and Methods". Equal amounts of proteins (40 μg) from each sample was resolved onto 10% polyacrylamide gels and analyzed by immunoblotting with each antibody indicated above. Arrows depict human tau expressed in PS19 mice. The mobilities of molecular mass markers are shown on the left.
Figures 2F, 2G, 2H, 2I:
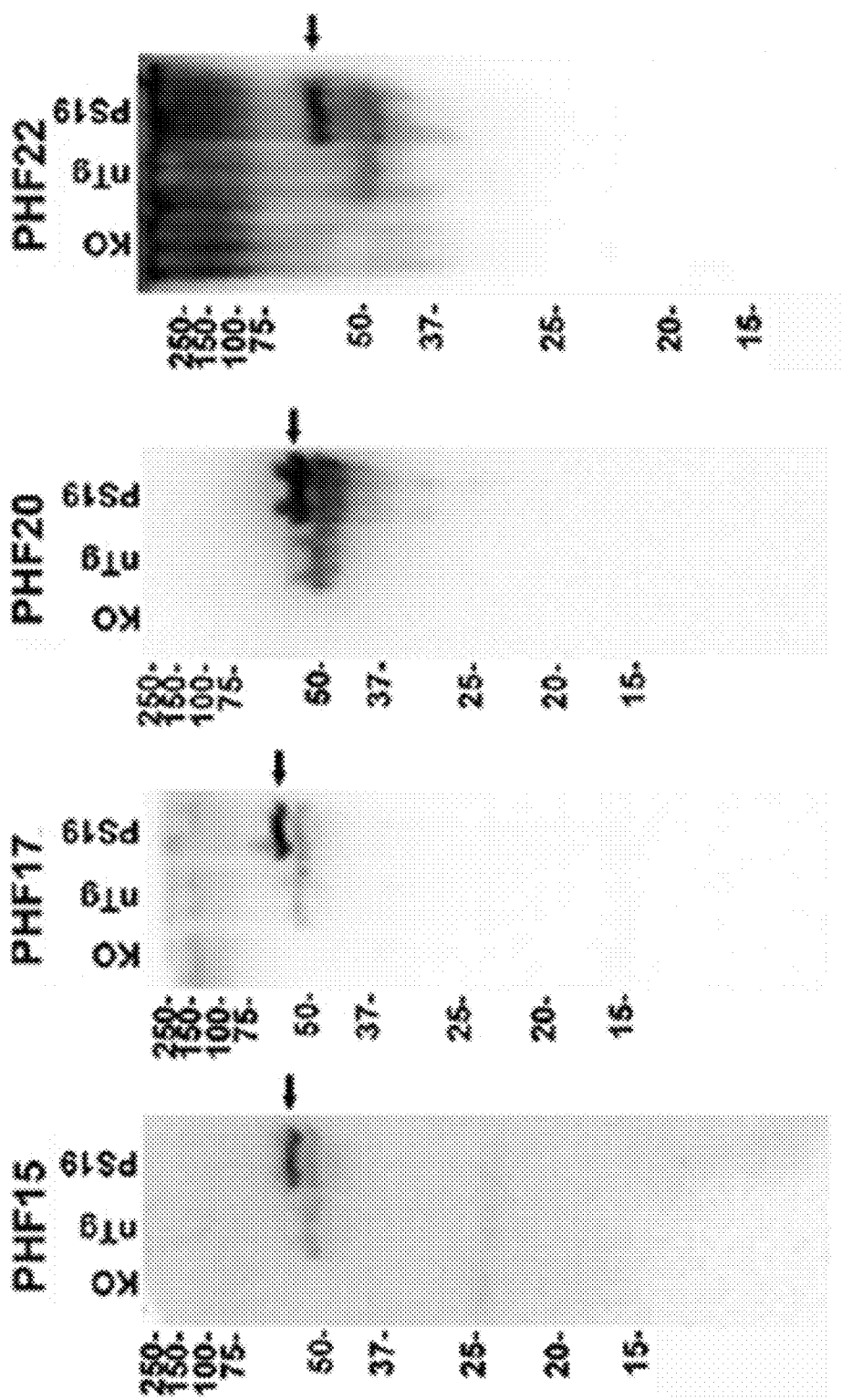
Figures 2J, 2K, 2L, 2M, 2N:
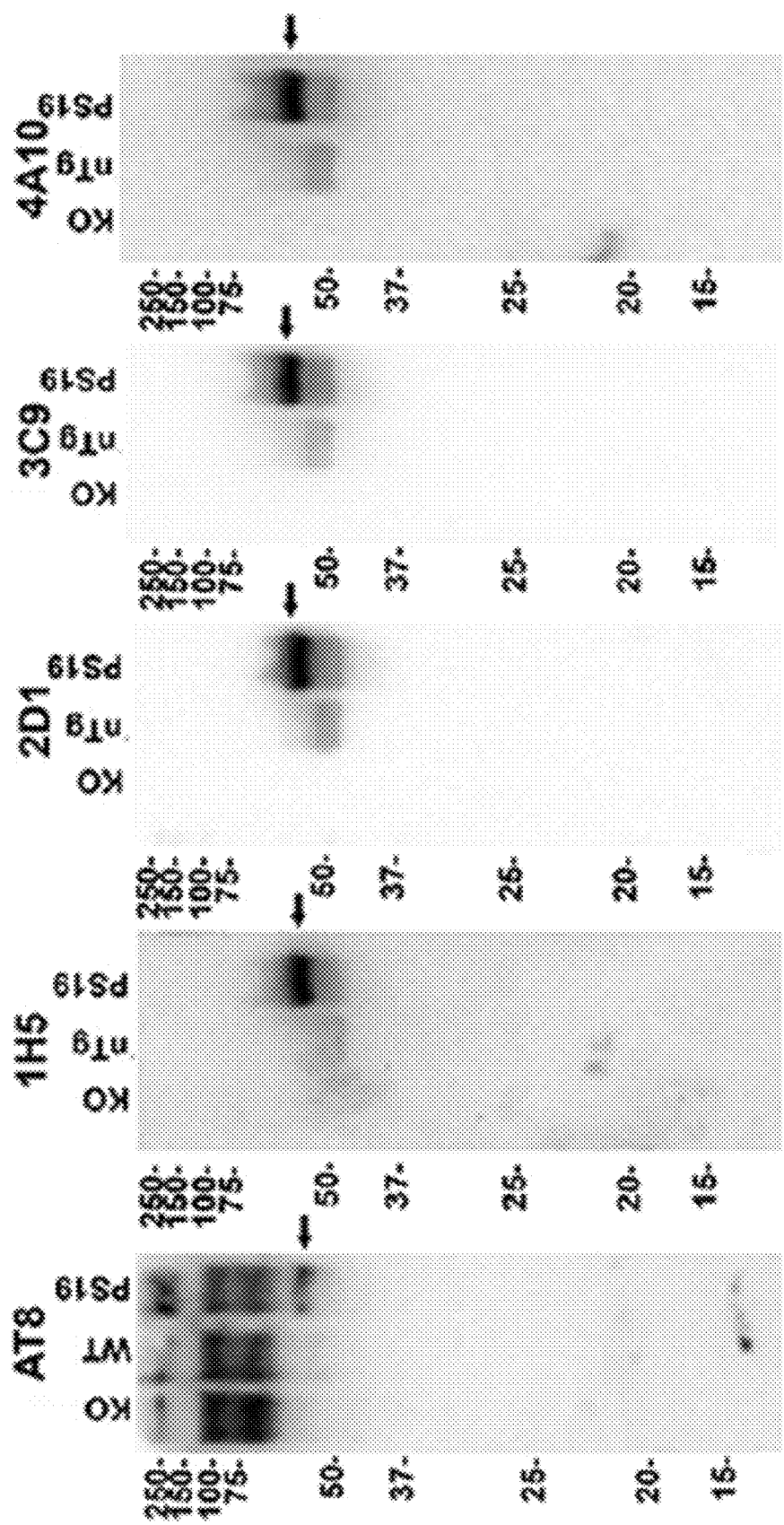
Figures 2O, 2P, 2Q, 2R, 2S:
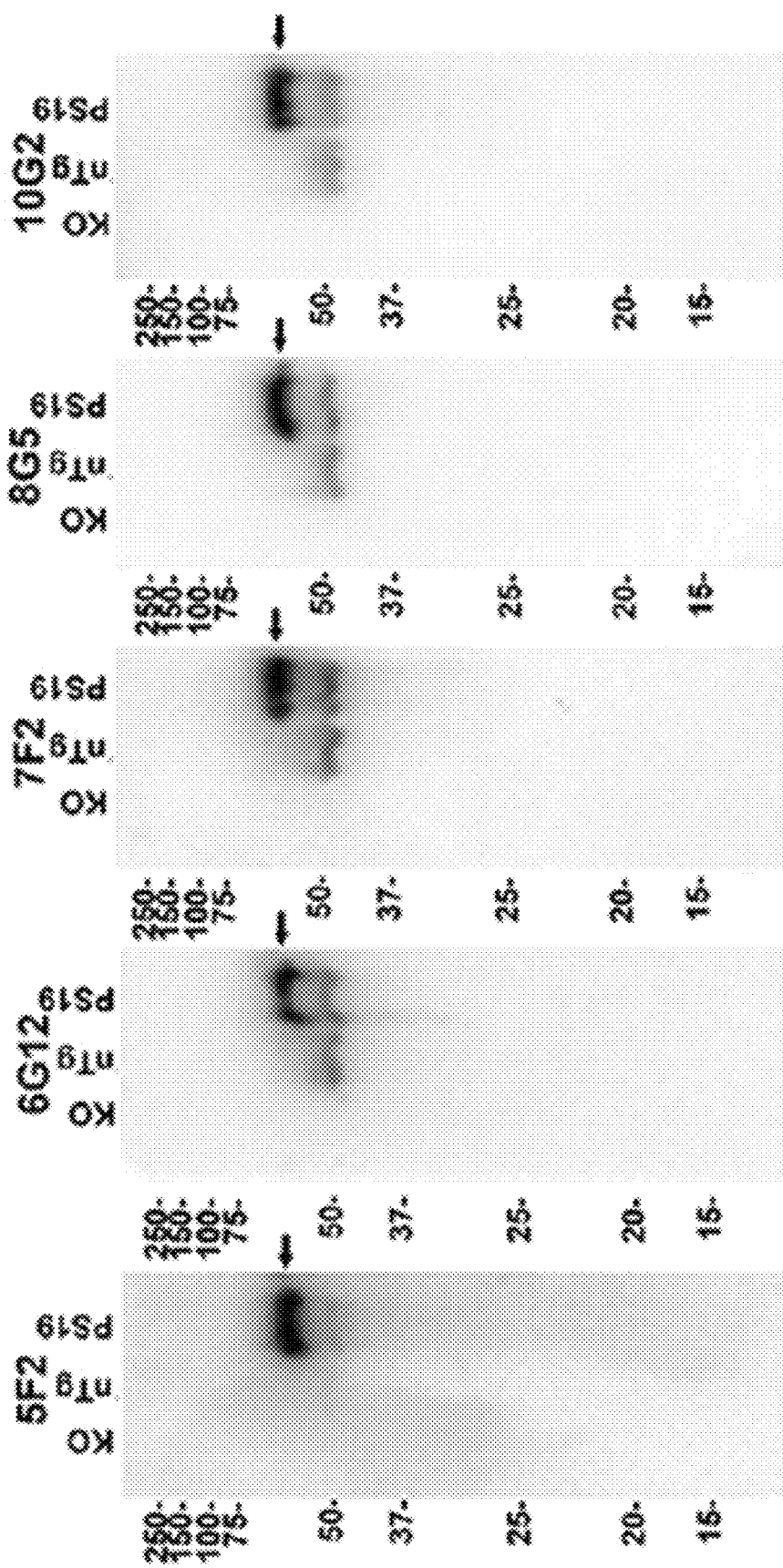
Figure 3A:
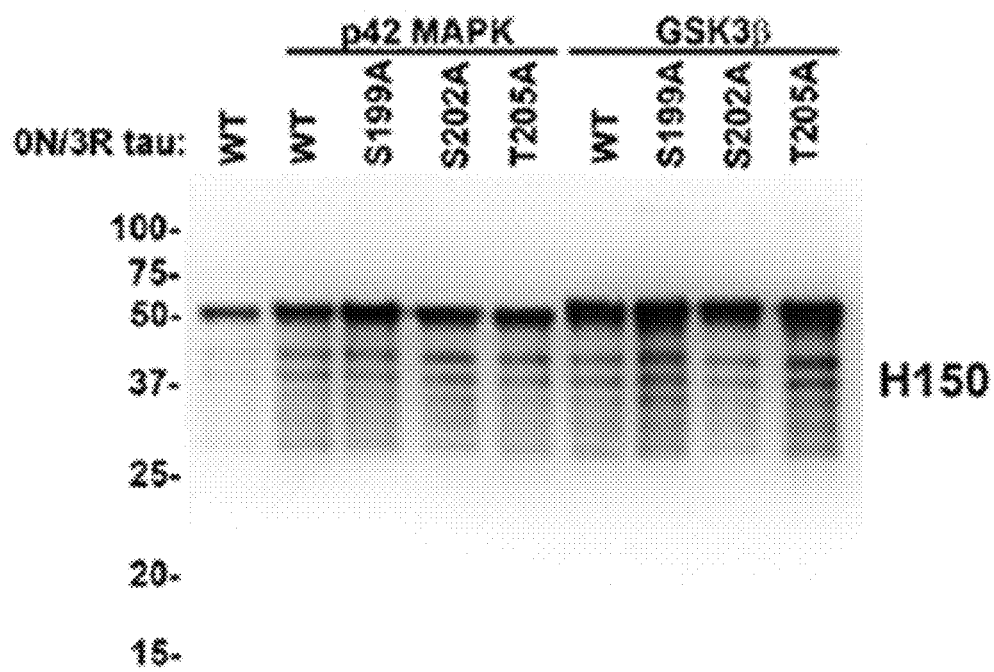
FIGS. 3A to 3J show specificity of tai antibodies raised against tau peptide p193-211 (SEQ ID NO: 4) as determined by immunoblotting with recombinant tau proteins phosphorylated in vitro with p42 MAPK or GSK3β. WT, S199A, S202A and T205A 0N/3R tau (mutants numbered according to 2N/4R human tau) were incubated with p42 MAPK or GSK3β or without any kinase as described in "Material and Methods". The proteins were resolved onto 10% polyacrylamide gels and analyzed by immunoblotting with the disclosed tau antibodies (as indicated above each blot) 1H5 (FIG. 3B), 2D1 (FIG. 3C), 3C9 (FIG. 3D), 4A10 (FIG. 3E), 5F2 (FIG. 3F), 6G12 (FIG. 3G), 7F2 (FIG. 3H), 8G5 (FIG. 3I), and 10G12 (FIG. 3J) and total tau antibody H150 (FIG. 3A). The mobilities of molecular mass markers are shown on the left.
Figure 3B:
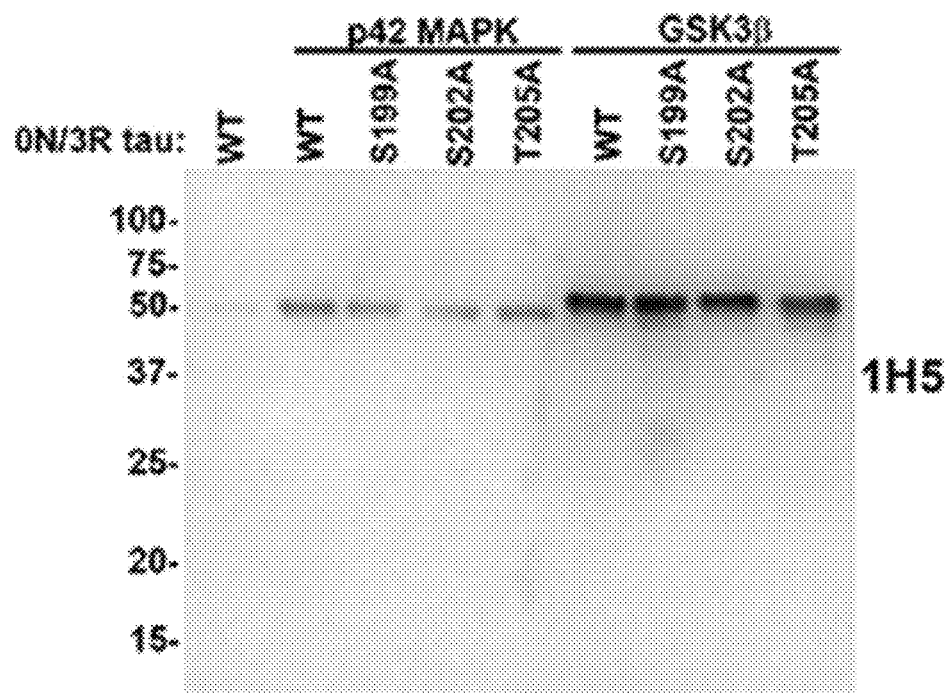
Figure 3C:
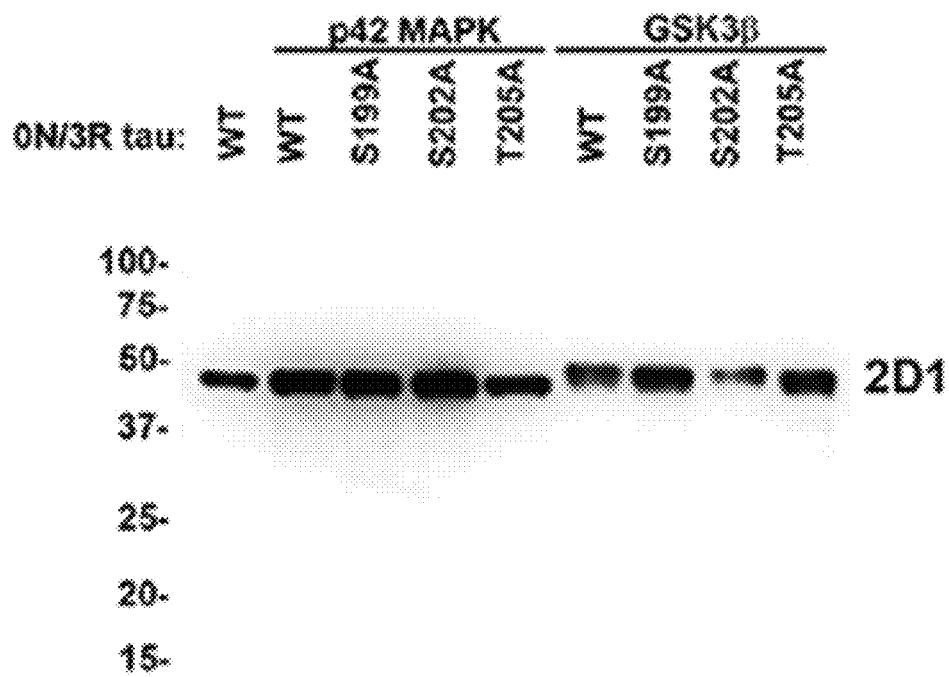
Figure 3D:
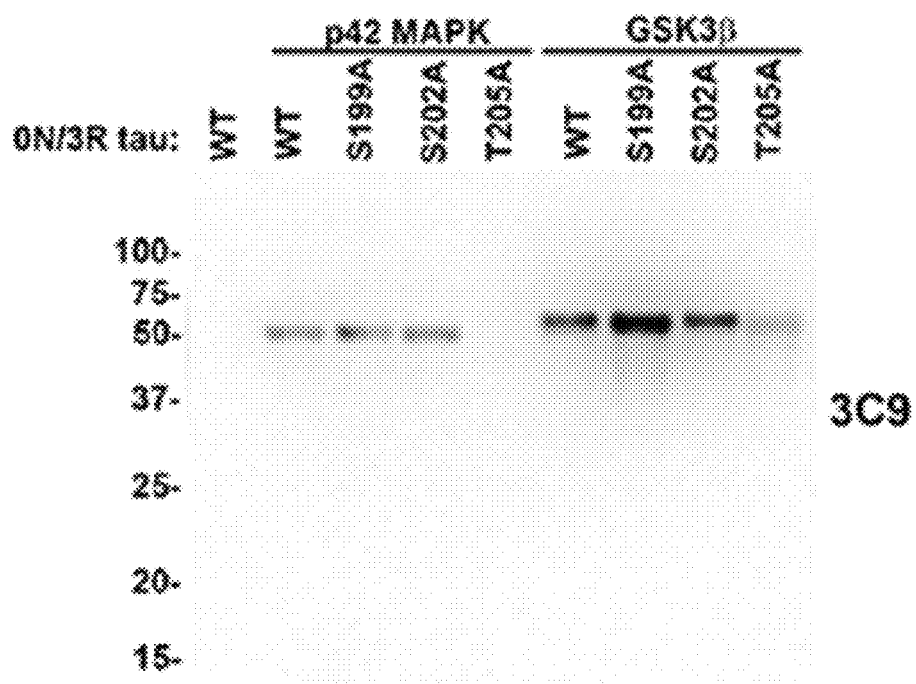
Figure 3E:
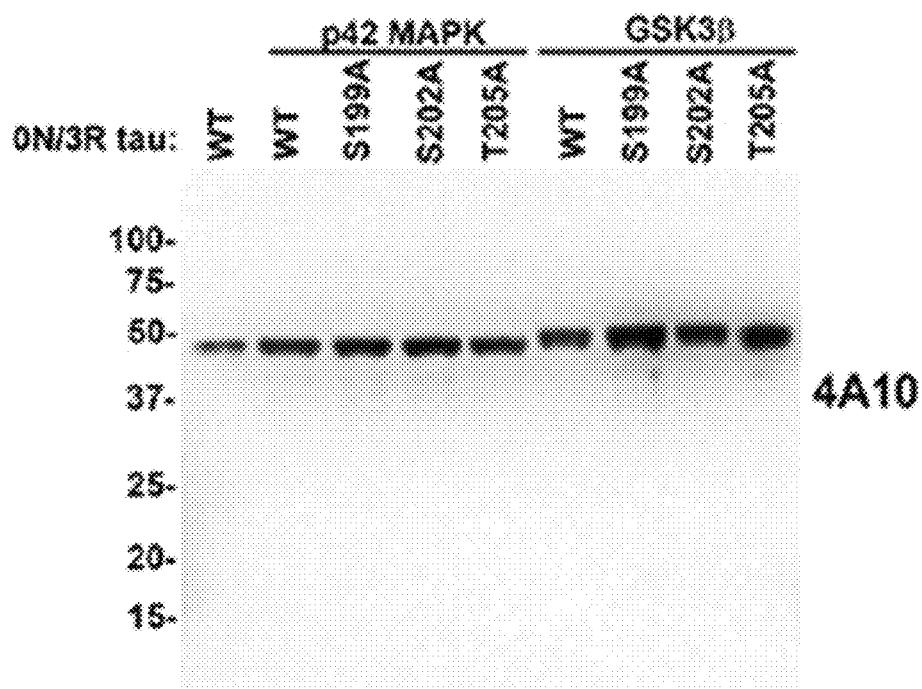
Figure 3F:
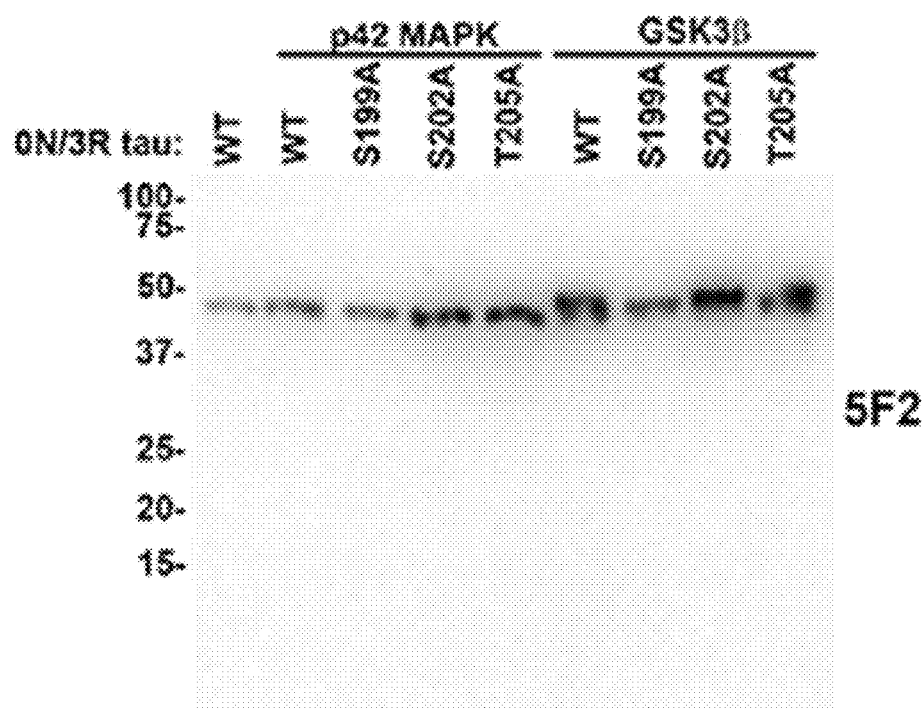
Figure 3G:
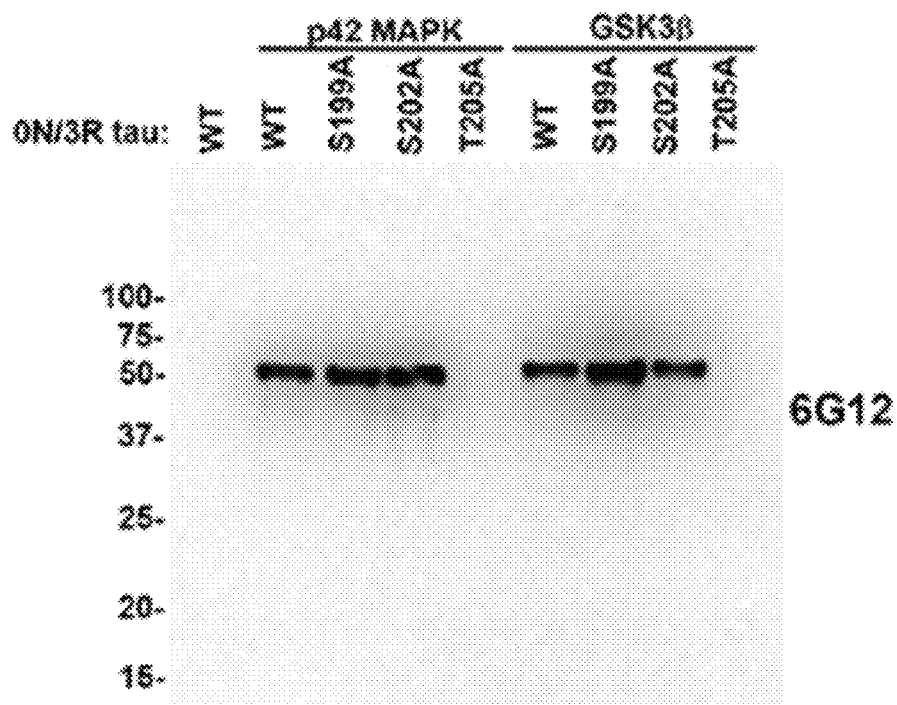
Figure 3H:
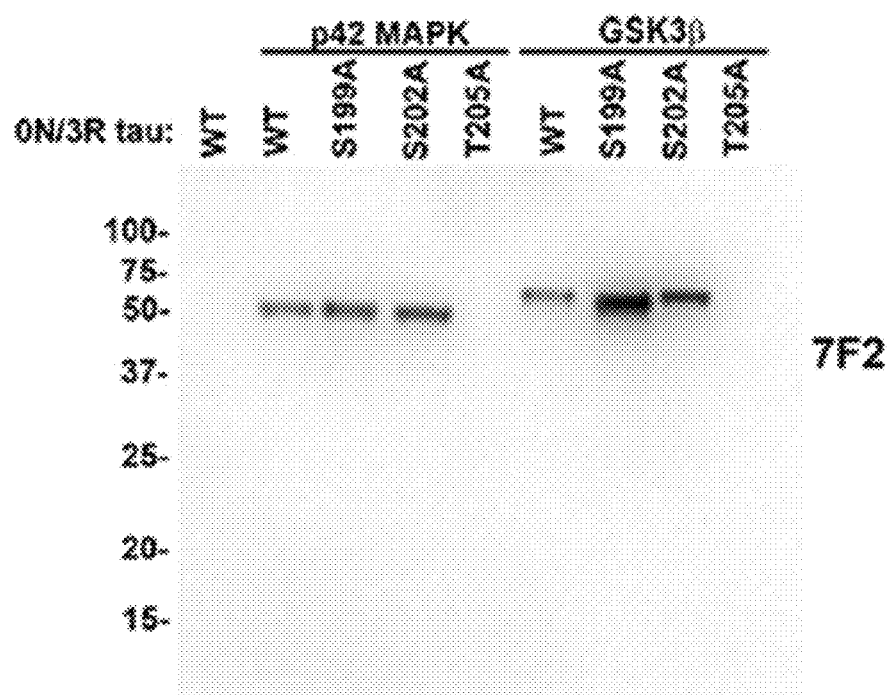
Figure 3I:
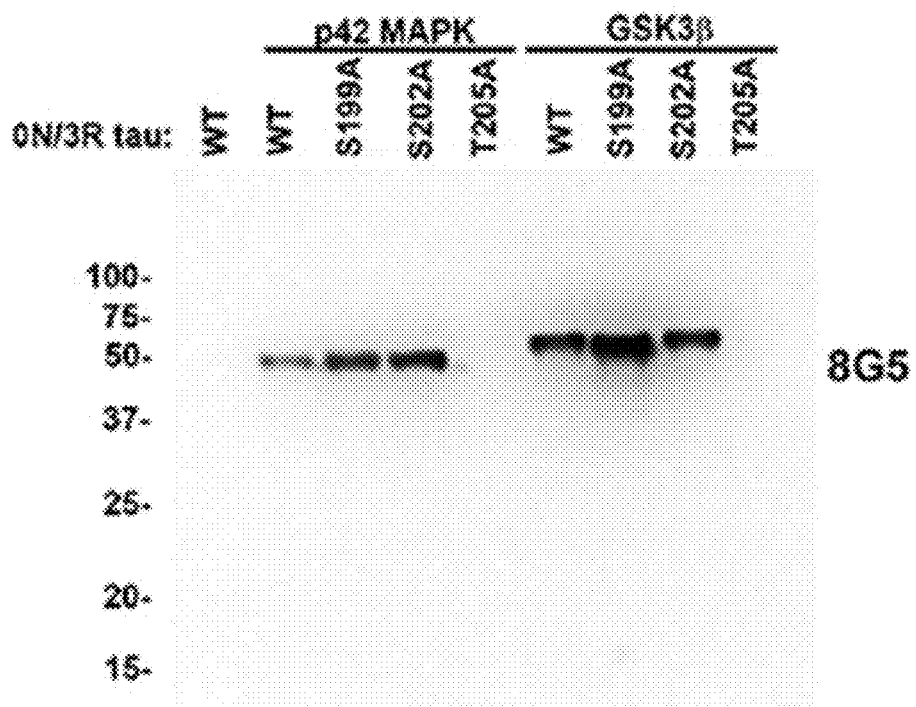
Figure 3J:
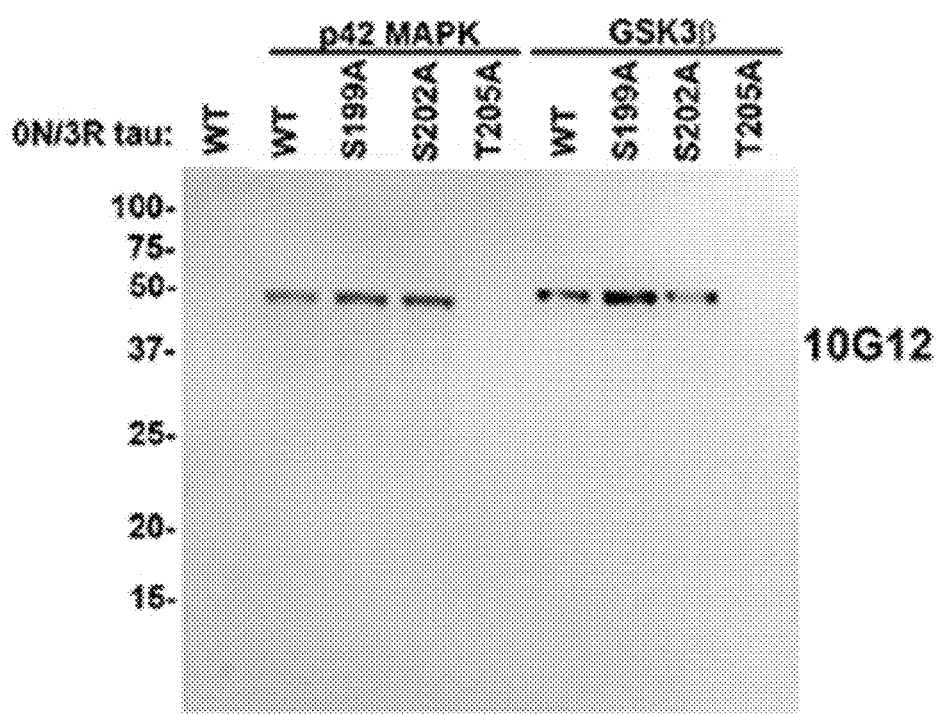

```
BRIEF DESCRIPTION OF THE SEQUENCES

SEQ ID NO: 1: Sequence of 2N/4R human tau.
MAEPRQEFEVMEDHAGTYGLGDRKDQGGYTMHQDQEGDTDAGLKESPLQTPTE
DGSEEPGSETSDAKSTPTAEDVTAPLVDEGAPGKQAAAQPHTEIPEGTTAEEAGIGD
TPSLEDEAAGHVTQARMVSKSKDGTGSDDKKAKGADGKTKIATPRGAAPPGQKGQ
ANATRIPAKTPPAPKTPPSSGEPPKSGDRSGYSSPGSPGTPGSRSRTPSLPTPPTR
EPKKVAVVRTPPKSPSSAKSRLQTAPVPMPDLKNVKSKIGSTENLKHQPGGGKVQII
NKKLDLSNVQSKCGSKDNIKHVPGGGSVQIVYKPVDLSKVTSKCGSLGNIHHKPGG
GQVEVKSEKLDFKDRVQSKIGSLDNITHVPGGGNKKIETHKLTFRENAKAKTDHGAE
IVYKSPVVSGDTSPRHLSNVSSTGSIDMVDSPQLATLADEVSASLAKQGL SEQ ID NO: 2: Sequence of 0N/3R human tau
MAEPRQEFEVMEDHAGTYGLGDRKDQGGYTMHQDQEGDTDAGLKAEEEAGIGDTP
SLEDEAAGHVTQARMVSKSKDGTGSDDKKAKGADGKTKIATPRGAAPPGQKGQA
NATRIPAKTPPAPKTPPSSGEPPKSGDRSGYSSPGSPGTPGSRSRTPSLPTPPTRE
PKKVAVVRTPPKSPSSAKSRLQTAPVPMPDLKNVKSKIGSTENLKHQPGGGKVQIV
YKPVDLSKVTSKCGSLGNIHHKPGGGQVEVKSEKLDFKDRVQSKIGSLDNITHVPG
GGNKKIETHKLTFRENAKAKTDHGAEIVYKSPVVSGDTSPRHLSNVSSTGSIDMVDS
PQLATLADEVSASLAKQGL SEQ ID NO: 3: Sequence of 391-409 of 2N/4R human tau with Cysteine
at C terminus
EIVYKSPVVSGDTSPRHLSC, where the residues at 6 and 14 are phosphorylated SEQ ID NO: 4: Sequence of 193-211 of 2N/4R human tau with Cysteine
at C terminus.
DRSGYSSPGSPGTPGSRSRC, where the residues at 7 and 10, and 13 are
phosphorylated SEQ ID NO: 5: Light chain sequence of antibody 2D1
DIVMSQSPSSLAVSAGEKVTMSCKSSQSLLYSRNQKNYLAWYQQRPGQSPKLLIY
WASSRESGVSDRFTGSGSGTDFTLTISSVKADDLAVYYCQQYYKSPLTFGAGTKLE
LKRADAAPTVSIFPPSSEQLTSGGASVV SEQ ID NO: 6: Heavy chain sequence of antibody 2D1.
EVKLVESGGGLVQPGGSLRLSCATSGFTFTDFSMNWVRQPPGKALEWLGCVRDR
AEGYTTEYSASVQGRFTISRDNSQSILYLQMNTLRPEDSATYYCARERAFAYWGQG
TLVTVSAAKTTPPSVYPLAPGSAA SEQ ID NO: 7: CDR1 sequence of light chain of antibody 2D1
KSSQSLLYSRNQKNYLA
```

| BRIEF DESCRIPTION OF THE SEQUENCES |
| --- |

SEQ ID NO: 8: CDR2 sequence of light chain of antibody 2D1
YWASSRES

SEQ ID NO: 9: CDR3 sequence of light chain of antibody 2D1
QQYYKSPLT

SEQ ID NO: 10: CDR1 sequence of heavy chain of antibody 2D1
ATSGFTFTDFSMN

SEQ ID NO: 11: CDR2 sequence of heavy chain of antibody 2D1
CVRDRAEGYTTE

SEQ ID NO: 12: CDR3 sequence of heavy chain of antibody 2D1
ARERAFA

SEQ ID NO: 13: Light chain sequence of antibody 7F2
EIVLTQSIPSLTVSAGERVTINCKSNQNLLWSGNQRYCLVWHQWKPGQTPTPLITWT
SDRYSGVPDRFIGGGSVTDFTLTISSVQAEDVALYFCQHHLHIPPWTFGGGTKLEIK
RADAAPTVSIFPPSSEQLTSGGASVV SEQ ID NO: 14: Heavy chain sequence of antibody 7F2
QVQLQQSGAELVQPGGSMKLSCVASGFTFSNYWMNWVRQSPETGLEWVAEIRLK
SYNYATHYAESVTGRFTISRDDSKNRVYLQMNNLGPDDTGIYYCTTGGAYHPFDY
WGQGTTLTVSSAKTTPPSVYPLAPGSAA SEQ ID NO: 15: CDR1 sequence of light chain of antibody 7F2
KSNQNLLWSGNQRYCLV SEQ ID NO: 16: CDR2 sequence of light chain of antibody 7F2
TWTSDRYS SEQ ID NO: 17: CDR3 sequence of light chain of antibody 7F2
QHHLHIPPWT SEQ ID NO: 18: CDR1 sequence of heavy chain of antibody 7F2
VASGFTFSNYWMN SEQ ID NO: 19: CDR2 sequence of heavy chain of antibody 7F2
EIRLKSYNYATH SEQ ID NO: 20: CDR3 sequence of heavy chain of antibody 7F2
TTGGAYHPFDY SEQ ID NO: 21: Light chain sequence of antibody PHF15
DILLTQSPAILSVSPGERDSFSCRASQNIGTSIHWYQQRTNGSPRLLIKYASESISGIP
SRFSGSGSGTDFTLSVNSVESEDVADYYCQQTKTWPTTFGAGTKLDLK SEQ ID NO: 22: Heavy chain sequence of antibody PHF15
EVQLVESGGGSVKPGGSLKLSCAASGFTFSSYALSWVRQTPEKRLEWVASITSGG
SYTYFPDSVKGRFTISRDNAKNTLYLQMSSLRSEDTAMYYCTRPGNYDGAWCAYW
GQGTLVTVSS SEQ ID NO: 23: CDR1 sequence of light chain of antibody PHF15
QNIGTS SEQ ID NO: 24: CDR2 sequence of light chain of antibody PHF15
YASX, where X is any amino acid (added so sequence is at least four amino acids)

SEQ ID NO: 25: CDR3 sequence of light chain of antibody PHF15
QQTKTWPTT

SEQ ID NO: 26: CDR1 sequence of heavy chain of antibody PHF15
GFTFSSYA

SEQ ID NO: 27: CDR2 sequence of heavy chain of antibody PHF15
ITSGGSYT

SEQ ID NO: 28: CDR3 sequence of heavy chain of antibody PHF15
TRPGN

SEQ ID NO: 29: Light chain sequence of antibody 10G12
DIVMSQSPSSLAVSVGEKVTMTCKSSQSLLYRNNQKNYLAWYQQKPGQSPKLLIYW
ASTRESGVPDRFTGSGSGTDFTLTISSVKAEDLAVYYCQQYYTYPYTFGGGTKLEIK
RADAAPTVSIFPPSSEQLTSGGASVV

| BRIEF DESCRIPTION OF THE SEQUENCES |
|---|
| SEQ ID NO: 30: Heavy chain sequence of antibody 10G12<br>EVKLEESGGGLVQPGGSMKLSCVASGFTFSNYWMNWVRQSPETGLEWVAEIRLK<br>SYNYATHYAESVTGRFTISRDDSKNRVYLQMNNLGPDDTGIYYCTTGGAYHPFDY<br>WGQGTTLTVSSAKTTPPSVYPLAPGSAA<br><br>SEQ ID NO: 31: CDR1 sequence of light chain of antibody 10G12<br>QSLLYRNNQKNY<br><br>SEQ ID NO: 32: CDR2 sequence of light chain of antibody 10G12<br>WAST<br><br>SEQ ID NO: 33: CDR3 sequence of light chain of antibody 10G12<br>QYYTYPYT<br><br>SEQ ID NO: 34: CDR1 sequence of heavy chain of antibody 10G12<br>GFTFSNYW<br><br>SEQ ID NO: 35: CDR2 sequence of heavy chain of antibody 10G12<br>IRLKSYNYAT<br><br>SEQ ID NO: 36: CDR3 sequence of heavy chain of antibody 10G12<br>TGGAY<br><br>SEQ ID NO: 37: Light chain sequence of antibody 6G12<br>DIVMSQSPSSLAVSVGEKVTLTCKSSRSLLYRGNQENFLAWYQQKPGQSPKLLIYW<br>ASTRESGVPDRFTGSGSGTDFTLTINSVKAEDLAVYYCQQYYTYPYTFGGGTKLEIK<br>RADAAPTVSIFPPSSEQLTSGGASVV<br><br>SEQ ID NO: 38: Heavy chain sequence of antibody 6G12<br>EVNLEESGGGLVQPGGSMKLSCVASGFTFSDYWMNWVRQSPEKGLEWVAEIRLK<br>SDNFATHYAESVKGRFTISRDDSKSSVYLQTNNLRAEDTGIYYCTLMRGDYGAEFAY<br>WGQGTLAIVSAAKTTPPSVYPLAPGSAA<br><br>SEQ ID NO: 39: CDR1 sequence of light chain of antibody 6G12<br>RSLLYRGNQENF<br><br>SEQ ID NO: 40: CDR2 sequence of light chain of antibody 6G12<br>WAST<br><br>SEQ ID NO: 41: CDR3 sequence of light chain of antibody 6G12<br>QYYTYPYT<br><br>SEQ ID NO: 42: CDR1 sequence of heavy chain of antibody 6G12<br>GFTFSDYW<br><br>SEQ ID NO: 43: CDR2 sequence of heavy chain of antibody 6G12<br>IRLKSDNFATH<br><br>SEQ ID NO: 44: CDR3 sequence of heavy chain of antibody 6G12<br>LMRGD<br><br>SEQ ID NO: 45: Light chain sequence of antibody 4A10<br>DIVLTQSPASLAVSLGQRATISYRASKSVSTSGYSYMHWNQQKPGQPPRLLIYLASN<br>LESGVPARFSGSGSGTDFTLNIHPVEEEDAATYYCQHIRELTRSEGGPSWKGAYTF<br>GGGTKLEIKRADAAPTVSIFPPSSEQLTSGGASVV<br><br>SEQ ID NO: 46: Heavy chain sequence of antibody 4A10<br>EVKLVESGGGLVQPGGSLRLSCATSGFTFTDFSMNWDRQPPGKALEWLGCVRDR<br>AEGYTTEYSASVQGRFTISRDNSQSILYLQMNTLRPEDSATYYCARERAFAYWGQG<br>TLVTVSAAKTTPPSVYPLAPGSAA<br><br>SEQ ID NO: 47: CDR1 sequence of light chain of antibody 4A10<br>KSVSTSGYSY<br><br>SEQ ID NO: 48: CDR2 sequence of light chain of antibody 4A10<br>LASN<br><br>SEQ ID NO: 49: CDR3 sequence of light chain of antibody 4A10<br>HIRELTRSEGGPSWKGAYT<br><br>SEQ ID NO: 50: CDR1 sequence of heavy chain of antibody 4A10<br>GFTFTDFS<br><br>SEQ ID NO: 51: CDR2 sequence of heavy chain of antibody 4A10<br>CVRDRA |

-continued

BRIEF DESCRIPTION OF THE SEQUENCES

SEQ ID NO: 52: CDR3 sequence of heavy chain of antibody 4A10
TYYCARERA

SEQ ID NO: 53: Light chain sequence of antibody PHF2
DILLTQSPAILSVSPGERVSFSCRASQNIGTSIHWYQQRTNGSPRLLIKYTSESISGIP
SRFGGSGSGTDFTLSVNGVESEDVADYYCQQTKTWPTTFGAGTKLELKR SEQ ID NO: 54: Heavy chain sequence of antibody PHF2
EVQLVESGGGSVKPGGSLKLSCAASGFTFSSYAMSWVRQTPEKRLEWVASITRGG
SYTYFPDSVKGRFTISRDNTKDTLYLQMSSLRSEDTAMYYCTRQGNYDGAWCDYW
GQGTLVTVSAA SEQ ID NO: 55: CDR1 sequence of light chain of antibody PHF2
QNIGTS SEQ ID NO: 56: CDR2 sequence of light chain of antibody PHF2
YTSX, where X is any amino acid (added so sequence is at least four amino acids)

SEQ ID NO: 57: CDR3 sequence of light chain of antibody PHF2
QQTKTWPTT

SEQ ID NO: 58: CDR1 sequence of heavy chain of antibody PHF2
GFTFSSYA

SEQ ID NO: 59: CDR2 sequence of heavy chain of antibody PHF2
ITRGGSYT

SEQ ID NO: 60: CDR3 sequence of heavy chain of antibody PHF2
TRQGN

DETAILED DESCRIPTION

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising".

The phrases "consisting essentially of" or "consists essentially of" indicate that the claim encompasses embodiments containing the specified materials or steps and those that do not materially affect the basic and novel characteristic(s) of the claim.

As used herein, the term "preventing" includes providing prophylaxis with respect to occurrence or recurrence of a particular disease, disorder, or condition in a subject. A subject may be predisposed to, susceptible to a particular disease, disorder, or condition, or at risk of developing such a disease, disorder, or condition, but has not yet been diagnosed with the disease, disorder, or condition.

As used herein, the term "treating" refers to clinical intervention designed to alter the natural course of a clinical pathology in A subject being treated. Desirable effects of treating a subject include decreasing the rate of progression, ameliorating or palliating the pathological state, and remission or improved prognosis of a particular disease, disorder, or condition. A subject is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the tau antibody to elicit a desired response in the subject.

A "subject" for purposes of treating or preventing refers to any animal, such as a mammal, including humans, domestic and farm animals, such as dogs, horses, rabbits, cattle, pigs, hamsters, gerbils, mice, ferrets, rats, or cats. In some embodiments, the subject is a human.

The term "antibody" is used here in a broad sense and covers a protein that includes an epitope recognition site. The term "antibody" includes polyclonal antibodies, monoclonal antibodies, murine monoclonal antibodies, human monoclonal antibodies, humanized antibodies, chimeric antibodies, human antibodies, intrabodies, antibody fragments (e.g., Fab, Fab'-SH, Fv, scFv, and F(ab')$_2$ fragments), antibodies having modified effector functions, fusion proteins containing an antibody portion, glycosylation variants of antibodies, amino acid sequence variants of antibodies, covalently modified antibodies, and any other modified configuration that includes an epitope recognition site.

The basic 4-chain antibody unit is a heterotetrameric glycoprotein composed of two identical light (L) chains and two identical heavy (H) chains. The pairing of a VH and VL together forms a single antigen-binding site. The structure and properties of the different classes of antibodies are described in the art, for example, in Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), antibodies belong to one of the five classes: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function. These subclasses in humans include: IgG1, IgG2, IgG3, IgG4, IgA1, and IgA2. The subunit structures and three dimensional configurations of different classes of antibodies are known in the art and are described in, for example, Abbas et al., Cellular and Molecular Immunology, 4.sup.th ed. (W.B. Saunders Co., 2000).

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains and is concentrated in three segments called complementarity determining region (CDR). CDRs are present in both in the light-chain and the heavy chain variable domains. The more highly conserved portions of variable domains are called the framework regions. The CDRs in each chain are held together in close proximity by the fragmework regions and, with the CDRs from the other chain, contribute to the formation of the antigen binding site of antibodies (see Kabat et al., Sequences of Immunological Interest, Fifth Edition, National Institute of Health, Bethesda, Md. (1991)). The constant domains are not directly involved in the binding of antibody to an antigen, but exhibit various effector functions, such as participation of the antibody in antibody-dependent-cellular toxicity.

The terms "full-length antibody", refer to an antibody in its substantially intact form, as opposed to an antibody fragment. Specifically full-length antibodies include those with heavy and light chains including an Fc region.

An "antibody fragment" comprises a portion of a full-length antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870; Zapata et al., Protein Eng. 8(10):1057-1062 (1995)); single-chain antibody molecules and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfide bonds. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in a non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "scFv" are antibody fragments that comprise the VH and VL antibody domains connected into a single polypeptide chain. In some embodiments, the scFv polypeptide further comprises a polypeptide linker between the VH and VL domains which enables the scFv to form the desired structure for antigen binding. For a review of the scFv, see Pluckthun in The Pharmacology of Monoclonal Antibodies, vol. 113, Rosenburg and Moore eds., Springer-Verlag, New York, pp. 269-315 (1994).

As used herein, a "chimeric antibody" refers to an antibody in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Nat'l Acad. Sci. USA, 81:6851-55 (1984)). As used herein, "humanized antibody" is used a subset of "chimeric antibodies".

"Humanized" forms of non-human (e.g., murine) antibodies are chimeric antibodies that contain minimal sequence derived from non-human immunoglobulin. In one embodiment, a humanized antibody is a human antibody (recipient antibody) in which residues from an CDR of the recipient are replaced by residues from an CDR of a non-human species (donor antibody) such as mouse, rat, rabbit or non-human primate having the desired specificity, affinity, and/or capacity. In some instances, framework residues of the human immunoglobulin are replaced by corresponding non-human residues.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues.

An "intrabody" is an antibody that is expressed within a cell to bind to an intracellular protein. Methods of preparing an intrabody that specifically recognizes a target protein are known in the art. For example, certain methods of producing and using intrabodies are provided by Marschall et al., mAbs, 2015, 7(6):2020-1035, which is hereby incorporated by reference in its entirety.

Typically, intrabodies are expressed within the target cell. Such expression can be accomplished by introduction into the target cell of a gene encoding an intrabody. Intrabodies can also be modified for intracellular localization when produced in cells other than target cells, such as prokaryotes or other suitable host cells. Intrabodies can remain in the cytoplasm. Intrabodies can also be introduced into the nucleii of target cells, for example, via a nuclear localization signal. Intrabodies can also undergo cotranslational translocation across the membrane into the lumen of the endoplasmic reticulum (ER). Translation and retention of intrabodies into the ER can be facilitated by a peptide sequence, for example, tetrapeptide Lys-Asp-Glu-Leu, which prevents the intrabody from being secreted from the ER. Stability and structure of intrabodies can be increased by one or techniques selected from the use of scFvs, modification of immunoglobulin VL domains for hyperstability, selection of antibodies resistant to the more reducing intracellular environment and expression as a fusion protein, for example, with a maltose binding protein or other stable intracellular proteins.

The term "complementarity determining region" or "CDR" when used herein refers to the regions of an antibody-variable domain that are hypervariable in sequence and/or form structurally defined loops. Generally, antibodies comprise six CDRs; three in the VH (H1, H2, H3), and three in the VL (L1, L2, L3). In native antibodies, H3 and L3 display the most diversity of the six CDRs, and H3 in particular is believed to play a unique role in conferring fine specificity to antibodies.

A number of CDR delineations are in use and are encompassed herein. The Kabat CDRs are based on sequence variability and are the most commonly used (Kabat et al.).

"Framework" residues are those variable-domain residues other than the CDR residues as herein defined.

As use herein, the term "specifically recognizes" refers to measurable and reproducible binding between an epitope and an antibody that is determinative of the presence of the epitope. For example, tau antibodies of the present disclosure specifically or preferentially bind specific tau epitopes with greater affinity, avidity, more readily, and/or with greater duration than it binds to other epitopes. An antibody that specifically or preferentially binds to a first epitope may or may not specifically or preferentially bind to a second epitope. As such, "specific recognition" does not necessarily require (although it can include) exclusive recognition. An antibody specifically binding to an antigen has the equilibrium dissociation constant ($K_D$) of lower than about $10^{-6}$ M, lower than about $10^{-9}$ M, or lower than about $10^{-12}$ M for the binding between the antibody and the corresponding antigen.

On the other hand, "non-specific binding" refers to the binding that is not based on specific interactions between an antibody and its corresponding antigen. Non-specific binding may result from non-specific interactions, such as, Van Der Waals forces. $K_D$ for the binding between the antibody and a non-specific antigen is typically higher than about $10^{-5}$ M, higher than about $10^{-4}$ M or higher than about $10^{-2}$ M.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. The boundaries of the Fc region of antibodies of different classes and subclasses are known in the art.

As used herein, "percent (%) amino acid sequence identity" and "homology" with respect to a sequence refers to the percentage of amino acid residues in a candidate sequence that are identical with the amino acid residues in the reference sequence. The sequence identity can be determined by the sequence alignment programs that are well known in the art. Non-limiting examples of such sequence alignment programs include, but are by not limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

The term "vector" as used herein, is intended to refer to a nucleic acid molecule capable of transporting another nucleic acid to which it has been linked. One type of vector is a "plasmid", which refers to a circular double stranded DNA into which additional DNA segments may be ligated. Other vectors include a viral vector, such as a phage vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

SEQ ID NO: 1 provided herein represents the sequence of 2N/4R human tau and SEQ ID NO: 2 provided herein represents the sequence of 0N/3R human tau. Throughout this disclosure, specific residues and positions are represented with respect to SEQ ID NO: 1. If in this specification or the claims an amino acid residue is indicated by an amino acid identification code and a residue position, such description corresponds to the amino acid and the specific position within SEQ ID NO: 1. For example, recitation of "Ser199" or "S199" indicates that the identified residue corresponds to the serine residue at $199^{th}$ position in SEQ ID NO: 1. Such nomenclature applies even if a fragment of SEQ ID NO: 1 is identified. For example, the phrase "Ser199 within SEQ ID NO: 4" indicates that the identified residue corresponds to the serine residue at 199th position in SEQ ID NO: 1 even if SEQ ID NO: 4 contains only nineteen amino acids. Sequence alignment of SEQ ID NO: 1 with the identified sequence can be performed to identify the referenced position.

Tauopathies are a group of neurodegenerative disorders, including Alzheimer's disease, defined by the presence of brain pathological inclusions comprised of abnormally aggregated and highly phosphorylated tau protein. The abundance of brain tau aggregates correlates with disease severity and certain phosphorylated-tau epitopes are increased at early stages of these diseases.

The microtubule-associated protein tau is hyperphosphorylated in the paired helical filaments (PHFs) of AD and several antibodies that specifically recognize certain epitopes and/or phosphorylation patterns of PHF are used for PHF detection. For example, antibody PHF-1 specifically recognizes tau peptides containing phosphorylated Ser396 and/or Ser404. PHF-1 exhibits more than 10-fold increase in the sensitivity of detection of tau peptides when both Ser396 and Ser404 are phosphorylated. Similarly, AT8 mouse monoclonal antibody recognizes tau peptides containing phosphorylated Ser199, Ser202, and Thr205. Additional tau antibodies having higher specificity and binding affinity towards phosphorylated epitopes compared to that of PHF1 and AT8 antibodies are desirable for therapeutic and diagnostic purposes.

Accordingly, certain embodiments of the disclosure provide tau antibodies or antigen binding fragments thereof that specifically recognize tau epitopes comprising phosphorylation at one or more of Ser199, Ser202, Thr205, Ser396, and Ser404. Particular embodiments of the disclosure provide tau antibodies or antigen binding fragments thereof that specifically recognize tau epitopes consisting of amino acid sequence of 391-409 of SEQ ID NO: 1 (which is SEQ ID NO: 3) and having phosphorylation at one or more of Ser396 and Ser404, preferably, both Ser396 and Ser404. Further embodiments of the disclosure provide tau antibodies or antigen binding fragments thereof that specifically recognize tau epitopes consisting of amino acid sequence of 193-211 of SEQ ID NO: 1 (which is SEQ ID NO: 4) and having phosphorylation at one or more of Ser199, Ser202, Thr205, preferably, all of Ser199, Ser202, and Thr205.

Tau antibodies or antigen binding fragments thereof disclosed herein specifically recognize tau epitopes comprising specific phosphorylation patterns and specifically recognize the tau protein with greater specificity and higher affinity than AT8 and PHF-1 antibodies. For example, in a Western blot analysis using whole brain extracts from unperfused mice, the tau antibodies or antigen binding fragments thereof disclosed herein do not specifically recognize any protein having a molecular weight of less than 37 Kd and greater than 75 Kd.

Particular embodiments of the disclosure provide phosphorylation independent tau antibodies and antigen binding fragments thereof that specifically recognize epitopes consisting of amino acid sequences of SEQ ID NO: 3 or 4. Phosphorylation independent tau antibodies or antigen binding fragments thereof specifically recognize their epitopes regardless of the phosphorylation status of the epitopes.

In certain embodiments, the disclosure provides antibodies or antigen binding fragments thereof that specifically recognize tau epitopes consisting of SEQ ID NO: 4 and comprising phosphorylation at one or more of Ser199, Ser202, and Thr205.

Certain embodiments of the disclosure provide antibodies or antigen binding fragments thereof that specifically recognize tau epitope consisting of SEQ ID NO: 4. In certain such embodiments, the antibody or antigen binding fragment thereof comprises light chain CDR1, CDR2, and CDR3 of SEQ ID NO: 7, 8, and 9, respectively. In further such embodiments, the antibody or antigen binding fragment thereof comprises heavy chain CDR1, CDR2, and CDR3 of SEQ ID NO: 10, 11, and 12, respectively. In some embodiments, the disclosure provides antibodies or antigen binding fragments thereof that specifically recognize tau epitope consisting of SEQ ID NO: 4, wherein the antibody comprises: light chain CDR1, CDR2, and CDR3 of SEQ ID NO: 7, 8, and 9, respectively and heavy chain CDR1, CDR2, and CDR3 of SEQ ID NO: 10, 11, and 12, respectively. For example, the disclosure provides an antibody that specifically recognizes tau epitope consisting of SEQ ID NO: 4, wherein the antibody comprises the light chain sequence of SEQ ID NO: 5 and the heavy chain sequence of SEQ ID NO: 6.

The antibodies or antigen binding fragments thereof having the light chain CDR1, CDR2, and CDR3 of SEQ ID NO: 7, 8, and 9, respectively, the heavy chain CDR1, CDR2, and CDR3 of SEQ ID NO: 10, 11, and 12, respectively, the light chain sequence of SEQ ID NO: 5, or the heavy chain sequence of SEQ ID NO: 6 can be the antibodies or antigen binding fragments thereof belonging to IgA, IgD, IgE, IgG, or IgM.

Certain embodiments of the disclosure provide antibodies or antigen binding fragments thereof that specifically recognize tau epitope consisting of SEQ ID NO: 4 and comprising or consisting of phosphorylation at Thr205. In certain such embodiments, the antibody or antigen binding fragment thereof comprises light chain CDR1, CDR2, and CDR3 of SEQ ID NO: 15, 16, and 17, respectively. In further such embodiments, the antibody or antigen binding fragment thereof comprises heavy chain CDR1, CDR2, and CDR3 of SEQ ID NO: 18, 19, and 20, respectively. In some embodiments, the disclosure provides antibodies that specifically recognize tau epitope consisting of SEQ ID NO: 4 and comprising phosphorylation at Thr205, wherein the antibody comprises: light chain CDR1, CDR2, and CDR3 of SEQ ID NO: 15, 16, and 17, respectively and heavy chain CDR1, CDR2, and CDR3 of SEQ ID NO: 18, 19, and 20, respectively. For example, the disclosure provides an antibody that specifically recognizes tau epitope consisting of SEQ ID NO: 4 and comprising phosphorylation at Thr205, wherein the antibody comprises the light chain sequence of SEQ ID NO: 13 and the heavy chain sequence of SEQ ID NO: 14.

The antibodies or antigen binding fragments thereof having the light chain CDR1, CDR2, and CDR3 of SEQ ID NO: 15, 16, and 17, respectively, the heavy chain CDR1, CDR2, and CDR3 of SEQ ID NO: 18, 19, and 20, respectively, the light chain sequence of SEQ ID NO: 13, or the heavy chain sequence of SEQ ID NO: 14 can be the antibodies or antigen binding fragments thereof belonging to IgA, IgD, IgE, IgG, or IgM.

Some embodiments of the disclosure provide antibodies or antigen binding fragments thereof that specifically recognize tau epitope consisting of SEQ ID NO: 3 and comprising or consisting of phosphorylation at Ser396 and Ser404. In certain such embodiments, the antibody or antigen binding fragment thereof comprises light chain CDR1, CDR2, and CDR3 of SEQ ID NO: 23, 24, and 25, respectively. In further such embodiments, the antibody or antigen binding fragment thereof comprises heavy chain CDR1, CDR2, and CDR3 of SEQ ID NO: 26, 27, and 28, respectively. In some embodiments, the disclosure provides antibodies that specifically recognize tau epitope consisting of SEQ ID NO: 3 and comprising phosphorylation at Ser396 and Ser404, wherein the antibody comprises: light chain CDR1, CDR2, and CDR3 of SEQ ID NO: 23, 24, and 25, respectively, and heavy chain CDR1, CDR2, and CDR3 of SEQ ID NO: 26, 27, and 28, respectively. For example, the disclosure provides an antibody that specifically recognizes tau epitope consisting of SEQ ID NO: 3 and comprising phosphorylation at Ser396 and Ser404, wherein the antibody comprises the light chain sequence of SEQ ID NO: 21 and the heavy chain sequence of SEQ ID NO: 22.

The antibodies or antigen binding fragments thereof having the light chain CDR1, CDR2, and CDR3 of SEQ ID NO: 23, 24, and 25, respectively, the heavy chain CDR1, CDR2, and CDR3 of SEQ ID NO: 26, 27, and 28, respectively, the light chain sequence of SEQ ID NO: 21, or the heavy chain sequence of SEQ ID NO: 22 can be the antibodies or antigen binding fragments thereof belonging to IgA, IgD, IgE, IgG, or IgM.

In certain such embodiments, the antibody or antigen binding fragment thereof comprises light chain CDR1, CDR2, and CDR3 of SEQ ID NO: 55, 56, and 57, respectively. In further such embodiments, the antibody or antigen binding fragment thereof comprises heavy chain CDR1, CDR2, and CDR3 of SEQ ID NO: 58, 59, and 60, respectively. For example, the disclosure provides an antibody that specifically recognizes tau epitope consisting of SEQ ID NO: 3 and comprising phosphorylation at Ser396 and Ser404, wherein the antibody comprises the light chain sequence of SEQ ID NO: 53 and the heavy chain sequence of SEQ ID NO: 54.

Further embodiments of the disclosure provide antibodies or antigen binding fragments thereof that specifically recognize tau epitope consisting of SEQ ID NO: 4 and comprising or consisting of phosphorylation at Thr205. In certain such embodiments, the antibody or antigen binding fragment thereof comprises light chain CDR1, CDR2, and CDR3 of SEQ ID NO: 31, 32, and 33, respectively. In further such embodiments, the antibody or antigen binding fragment thereof comprises heavy chain CDR1, CDR2, and CDR3 of SEQ ID NO: 34, 35, and 36, respectively. In some embodiments, the disclosure provides antibodies that specifically recognize tau epitope consisting of SEQ ID NO: 4 and comprising phosphorylation at Thr205, wherein the antibody comprises: light chain CDR1, CDR2, and CDR3 of SEQ ID NO: 31, 32, and 33, respectively and heavy chain CDR1, CDR2, and CDR3 of SEQ ID NO: 34, 35, and 36, respectively. For example, the disclosure provides an antibody that specifically recognizes tau epitope consisting of SEQ ID NO: 4 and comprising phosphorylation at Thr205, wherein the antibody comprises the light chain sequence of SEQ ID NO: 29 and the heavy chain sequence of SEQ ID NO: 30.

The antibodies or antigen binding fragments thereof having the light chain CDR1, CDR2, and CDR3 of SEQ ID NO: 31, 32, and 33, respectively, the heavy chain CDR1, CDR2, and CDR3 of SEQ ID NO: 34, 35, and 36, respectively, the light chain sequence of SEQ ID NO: 29, or the heavy chain sequence of SEQ ID NO: 30 can be the antibodies or antigen binding fragments thereof belonging to IgA, IgD, IgE, IgG, or IgM.

Certain embodiments of the disclosure provide antibodies or antigen binding fragments thereof that specifically recognize tau epitope consisting of SEQ ID NO: 4 and comprising or consisting of phosphorylation at Thr205. In certain such embodiments, the antibody or antigen binding fragment thereof comprises light chain CDR1, CDR2, and CDR3 of SEQ ID NO: 39, 40, and 41, respectively. In further such embodiments, the antibody or antigen binding fragment thereof comprises heavy chain CDR1, CDR2, and CDR3 of SEQ ID NO: 42, 43, and 44, respectively. In some embodiments, the disclosure provides antibodies that specifically recognize tau epitope consisting of SEQ ID NO: 4 and comprising phosphorylation at Thr205, wherein the antibody comprises: light chain CDR1, CDR2, and CDR3 of SEQ ID NO: 39, 40, and 41, respectively, and heavy chain CDR1, CDR2, and CDR3 of SEQ ID NO: 42, 43, and 44, respectively. For example, the disclosure provides an antibody that specifically recognizes tau epitope consisting of SEQ ID NO: 4 and comprising phosphorylation at Thr205, wherein the antibody comprises the light chain sequence of SEQ ID NO: 37 and the heavy chain sequence of SEQ ID NO: 38.

The antibodies or antigen binding fragments thereof having the light chain CDR1, CDR2, and CDR3 of SEQ ID NO: 39, 40, and 41, respectively, the heavy chain CDR1, CDR2, and CDR3 of SEQ ID NO: 42, 43, and 44, respectively, the light chain sequence of SEQ ID NO: 37, or the heavy chain sequence of SEQ ID NO: 38 can be the antibodies or antigen binding fragments thereof belonging to IgA, IgD, IgE, IgG, or IgM.

Even further embodiments of the disclosure provide antibodies or antigen binding fragments thereof that specifically recognize tau epitope consisting of SEQ ID NO: 4. In certain such embodiments, the antibody or antigen binding fragment thereof comprises light chain CDR1, CDR2, and CDR3 of SEQ ID NO: 47, 48, and 49, respectively. In further such embodiments, the antibody or antigen binding fragment thereof comprises heavy chain CDR1, CDR2, and CDR3 of SEQ ID NO: 50, 51, and 52, respectively. In some embodiments, the disclosure provides antibodies that specifically recognize tau epitope consisting of SEQ ID NO: 4, wherein the antibody comprises: light chain CDR1, CDR2, and CDR3 of SEQ ID NO: 47, 48, and 49, respectively, and heavy chain CDR1, CDR2, and CDR3 of SEQ ID NO: 50, 51, and 52, respectively. For example, the disclosure provides an antibody that specifically recognizes tau epitope consisting of SEQ ID NO: 4, wherein the antibody comprises the light chain sequence of SEQ ID NO: 45 and the heavy chain sequence of SEQ ID NO: 46.

The antibodies or antigen binding fragments thereof having the light chain CDR1, CDR2, and CDR3 of SEQ ID NO: 47, 48, and 49, respectively, the heavy chain CDR1, CDR2, and CDR3 of SEQ ID NO: 50, 51, and 52, respectively, the light chain sequence of SEQ ID NO: 45, or the heavy chain sequence of SEQ ID NO: 46 can be the antibodies or antigen binding fragments thereof belonging to IgA, IgD, IgE, IgG, or IgM.

In some embodiments, the disclosure provides tau antibodies or antigen binding fragments thereof comprising a light chain domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 5, 13, 21, 29, 37 or 45. In specific embodiments, tau antibodies or antigen binding fragments thereof having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5, 13, 21, 29, 37 or 45 do not have any amino acid variants in the CDR sequences of SEQ ID NOs: 7-9, 15-17, 23-25, 31-33, 39-41 or 47-49, respectively.

In other embodiments, the disclosure provides tau antibodies or antigen binding fragments thereof comprising a heavy chain variable domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 6, 14, 22, 30, 38 or 46. In specific embodiments, the tau antibodies or antigen binding fragments thereof having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6, 14, 22, 30, 38 or 46 do not have any amino acid variants in the CDR sequences of SEQ ID NOs: 10-12, 18-20, 26-28, 34-36, 42-44 or 50-52, respectively.

Further embodiments of the disclosure provide tau antibodies or antigen binding fragments thereof, comprising: a light chain variable domain and/or a heavy chain variable domain, wherein the light chain variable domain comprises the CDRs of a light chain variable domain of a monoclonal antibody selected from PHF2, PHF15, PFH17, PHF20, PHF22, 1H5, 2D1, 3C9, 4A10, 5F2, 6G12, 7F2, 8G5, and 10G12 and/or the heavy chain variable domain comprises the CDRs of a heavy chain variable domain of a monoclonal antibody selected from PHF2, PHF15, PFH17, PHF20, PHF22, 1H5, 2D1, 3C9, 4A10, 5F2, 6G12, 7F2, 8G5, and 10G12.

In certain such embodiments, the disclosure provides tau antibodies or antigen binding fragments thereof, comprising: a light chain variable domain and a heavy chain variable domain, wherein the light chain variable domain comprises the CDRs of a light chain variable domain of a monoclonal antibody selected from PHF2, PHF15, PFH17, PHF20, PHF22, 1H5, 2D1, 3C9, 4A10, 5F2, 6G12, 7F2, 8G5, and 10G12 and the heavy chain variable domain comprises the CDRs of a heavy chain variable domain of a monoclonal antibody selected from PHF2, PHF15, PFH17, PHF20, PHF22, 1H5, 2D1, 3C9, 4A10, 5F2, 6G12, 7F2, 8G5, and 10G12.

In further such embodiments, tau antibodies or antigen binding fragments thereof, comprise: a light chain variable domain and/or a heavy chain variable domain, wherein the light chain variable domain comprises the CDRs of a light chain variable domain of a monoclonal antibody selected from PHF2, PHF15, PFH17, PHF20, and PHF22 and/or the heavy chain variable domain comprises the CDRs of a heavy chain variable domain of a monoclonal antibody selected from PHF2, PHF15, PFH17, PHF20, and PHF22.

In particular embodiments, tau antibodies or antigen binding fragments thereof, comprise: a light chain variable domain and/or a heavy chain variable domain, wherein the light chain variable domain comprises the CDRs of a light chain variable domain of a monoclonal antibody selected from 2D1, 3C9, 4A10, 5F2, 6G12, 7F2, 8G5, and 10G12 and/or the heavy chain variable domain comprises the CDRs of a heavy chain variable domain of a monoclonal antibody selected from 1H5, 2D1, 3C9, 4A10, 5F2, 6G12, 7F2, 8G5, and 10G12.

Binding specificities of the monoclonal antibodies are provided in Table 1 below:

TABLE 1

Summary of tau monoclonal antibodies. Listed are the antigens used to generate each antibody, the specificity for each antibody, and their isotypes.
(ND: not determined)

| Antibody | Antigen | Specificity | Isotype |
|---|---|---|---|
| PHF2 | $^{391}$EIVYKpSPVVSGDTpSPR HLS$^{409}$ (SEQ ID NO: 3) | phosphorylated pS396/S404 | IgG$_1$ |
| PHF15 | $^{391}$EIVYKpSPVVSGDTpSPR HLS$^{409}$ (SEQ ID NO: 3) | phosphorylated pS396/S404 | IgG$_1$ |
| PFH17 | $^{391}$EIVYKpSPVVSGDTpSPR HLS$^{409}$ (SEQ ID NO: 3) | phosphorylated pS396/S404 | ND |
| PHF20 | $^{391}$EIVYKpSPVVSGDTpSPR HLS$^{409}$ (SEQ ID NO: 3) | phosphorylated S404 | IgG$_{2B}$ |
| PHF22 | $^{391}$EIVYKpSPVVSGDTpSPR HLS$^{409}$ (SEQ ID NO: 3) | phosphorylated S396/S404 | IgG$_1$ |
| 1H5 | $^{193}$DRSGYSpSPGpSPGpTP GSRSR$^{211}$ (SEQ ID NO: 4) | prefers phosphorylated tau | IgM |
| 2D1 | $^{193}$DRSGYSpSPGpSPGpTP GSRSR$^{211}$ (SEQ ID NO: 4) | phosphorylation independent | IgG$_1$ |
| 3C9 | $^{193}$DRSGYSpSPGpSPGpTP GSRSR$^{211}$ (SEQ ID NO: 4) | prefers phosphorylated T205 | IgG$_1$ |
| 4A10 | $^{193}$DRSGYSpSPGpSPGpTP GSRSR$^{211}$ (SEQ ID NO: 4) | phosphorylation-independent | IgG$_1$ |
| 5F2 | $^{193}$DRSGYSpSPGpSPGpTP GSRSR$^{211}$ (SEQ ID NO: 4) | phosphorylation-independent | IgG$_1$ |
| 6G12 | $^{193}$DRSGYSpSPGpSPGpTP GSRSR$^{211}$ (SEQ ID NO: 4) | phosphorylated T205 | IgG$_1$ |

TABLE 1-continued

Summary of tau monoclonal antibodies. Listed are the antigens used to generate each antibody, the specificity for each antibody, and their isotypes.
(ND: not determined)

| Antibody | Antigen | Specificity | Isotype |
|---|---|---|---|
| 7F2 | $^{193}$DRSGYSpSPGpSPGpTP GSRSR$^{211}$ (SEQ ID NO: 4) | phosphorylated T205 | IgG$_1$ |
| 8G5 | $^{193}$DRSGYSpSPGpSPGpTP GSRSR$^{211}$ (SEQ ID NO: 4) | phosphorylated T205 | IgG$_1$ |
| 10G12 | $^{193}$DRSGYSpSPGpSPGpTP GSRSR$^{211}$ (SEQ ID NO: 4) | phosphorylated T205 | IgG$_1$ |

Antibody Preparation

Tau antibodies of the present disclosure include polyclonal antibodies or monoclonal antibodies. Monoclonal antibodies can be murine monoclonal antibodies, human monoclonal antibodies, humanized antibodies, chimeric antibodies, human antibodies, intrabodies, antibody fragments (e.g., Fab, Fab'-SH, Fv, scFv, and F(ab')$_2$ fragments), antibodies having modified effector functions, fusion proteins containing an antibody portion, glycosylation variants of antibodies, amino acid sequence variants of antibodies, covalently modified antibodies, and any other modified configuration of a protein that includes an epitope recognition site, such as an epitope consisting of amino acid sequence of SEQ ID NO: 3 or 4. The tau antibodies can be human, murine, rat, or of any other origin (including chimeric or humanized antibodies).

Polyclonal tau antibodies are generally raised in animals by multiple subcutaneous (sc) or intraperitoneal (ip) injections of the relevant epitopes and an adjuvant. The relevant epitope can be conjugated to a protein that is immunogenic in the species to be immunized. Examples of such proteins include KLH, serum albumin, bovine thyroglobulin, or soybean trypsin inhibitor. Such conjugation can be performed using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl$_2$, or R$_1$N=C=NR, where R and R$_1$ are independently lower alkyl groups. Examples of adjuvants which may be employed include Freund's complete adjuvant and MPL-TDM adjuvant (monophosphoryl Lipid A, synthetic trehalose dicorynomycolate). Conjugates also can be made in recombinant-cell culture as protein fusions. Appropriate immunization protocols are known to a skilled artisan and such embodiments are within the purview of the disclosure.

The animals can be immunized against the desired antigen, immunogenic conjugates, or derivatives by combining appropriate amounts of epitopes or epitope conjugates (e.g., 100 μg for rabbits or 5 μg for mice) with appropriate amount (e.g., 3 times the weight) of Freund's complete adjuvant and injecting the solution intradermally at multiple sites. Also, aggregating agents such as alum are suitable to enhance the immune response. After an appropriate duration of time, such as about one month, the animals can be boosted with about one-fifth or one-tenth of the original amount of peptide or conjugate in Freund's complete adjuvant by subcutaneous injection at multiple sites. Seven to fourteen days later, the animals can be bled and the serum can be assayed for antibody titer. Animals can be further boosted with the epitope until the antibody titer plateaus.

Monoclonal tau antibodies are a population of substantially homogeneous antibodies, i.e., the individual antibodies comprising the population are identical except for possible naturally occurring mutations and/or post-translational modifications (e.g., isomerizations, amidations) that may be present in minor amounts. Thus, "monoclonal antibodies" do not comprise a mixture of discrete antibodies. For example, the monoclonal tau antibodies can be made using the hybridoma method described by Kohler et al., Nature, 256:495 (1975), or may be made by recombinant DNA methods (U.S. Pat. No. 4,816,567). Methods of producing hybridoma cell lines producing antibodies of interest are well known in the art and such embodiments are within the purview of the disclosure.

Monoclonal antibodies that specifically recognize tau epitopes can also be made by recombinant DNA methods, such as those disclosed in U.S. Pat. No. 4,816,567. DNA encoding the monoclonal antibodies is isolated and sequenced using conventional procedures (e.g., by using oligonucleotide probes that specifically bind to genes encoding the heavy and light chains of murine antibodies). The hybridoma cells can serve as a source of such DNA. To synthesize monoclonal antibodies, the isolated DNA can be placed into expression vectors, which are then transfected into host-cells such as *Escherichia coli* cells, simian COS cells, Chinese hamster ovary (CHO) cells, or myeloma cells that do not otherwise produce an antibody. Methods of expressing antibodies in host cells of interest are known in the art and such embodiments are within the purview of the disclosure.

In certain embodiments, tau antibodies can be isolated from antibody phage libraries. Methods of generating monoclonal antibodies using phage libraries are known in the art and such embodiments are within the purview of the disclosure.

The DNA encoding antibodies or fragments thereof may be modified, for example, by substituting the coding sequence for human heavy- and light-chain constant domains in place of the homologous murine sequences. Certain examples of such techniques are described in U.S. Pat. No. 4,816,567; Morrison, et al., Proc. Natl Acad. Sci. USA, 81:6851 (1984). The DNA encoding antibodies or fragments thereof may also be covalently joined the coding sequence for a non-antibody polypeptide. Typically such non-antibody polypeptides are substituted for the constant domains of an antibody. Alternatively, the constant domains of antibodies can be substituted for the variable domains of antibodies having different epitope specificity to create a chimeric bivalent antibody comprising multiple antigen binding sites having multiple and different specificity.

The monoclonal antibodies described herein can be monovalent, the preparation of which is well known in the art, for example, recombinant expression of antibody light chain and a modified heavy chain. The heavy chain is truncated generally at any point in the Fc region to prevent heavy chain crosslinking. Alternatively, the relevant cysteine residues may be substituted with another amino acid residue or are deleted to prevent crosslinking. In vitro methods are also suitable for preparing monovalent antibodies. Digestion of antibodies to produce fragments thereof, particularly Fab fragments, can be accomplished using techniques known in the art.

Chimeric or hybrid tau antibodies also may be prepared in vitro using known methods in the art, for example, using crosslinking agents. For example, immunotoxins may be constructed using a disulfide-exchange reaction or by forming a thioether bond. Examples of suitable reagents for this purpose include iminothiolate and methyl-4-mercaptobutyrimidate.

Humanized Antibodies

Tau antibodies or antibody fragments thereof of the present disclosure further include humanized or human antibodies. Humanized antibodies are chimeric antibodies or fragments that contain minimal sequence derived from non-human antibodies. Humanized antibodies include human antibodies (recipient antibodies) in which CDRs of the human (recipient) antibodies are replaced by CDRs of a non-human species (donor antibody) such as mouse, rat, or rabbit having the desired specificity, affinity and capacity. In some instances, Fv framework residues of the human antibodies are replaced by corresponding non-human portions. Humanized antibodies may also comprise residues which are found neither in the recipient antibody nor in the imported CDRs or framework sequences. In general, the humanized antibodies comprise substantially all of at least one, and typically two, variable domains, in which all or substantially all of the CDRs correspond to those of the non-human antibodies and all or substantially all of the FR regions are those of the human antibodies. The humanized antibodies can also comprise at least a portion of the Fc region, typically of a human Fc. As such, humanized antibodies are chimeric antibodies (U.S. Pat. No. 4,816,567).

In some embodiments, the tau antibody is a chimeric antibody comprising the heavy and light chain variable domains of any of the tau antibodies described herein (e.g., antibodies PHF2, PHF15, PFH17, PHF20, PHF22, 1H5, 2D1, 3C9, 4A10, 5F2, 6G12, 7F2, 8G5, 10G12) and constant regions from a human antibody.

The choice of human variable domains, both light and heavy, to be used in making the humanized antibodies dictates antigenicity of the humanized antibodies in humans. Typically, the sequence of the variable domain of a rodent antibody is screened against the entire library of known human variable-domain sequences. The human sequence which is closest to that of the rodent is then accepted as the human framework for the humanized antibody. Sims et al., J. Immunol., 151:2296 (1993); Chothia et al., J. Mol. Biol., 196:901 (1987). Alternatively, a particular framework derived from the consensus sequence of all human antibodies of a particular subgroup of light or heavy chains can be used. The same framework may be used for several different humanized antibodies. Carter et al., Proc. Nat'l Acad. Sci. USA 89:4285 (1992); Presta et al., J. Immunol. 151:2623 (1993).

Furthermore, humanized antibodies are designed to retain high affinity for the epitope and other favorable biological properties. To that end, humanized antibodies are prepared by analyzing the parental sequences and various conceptual humanized products using three-dimensional models of the parental and humanized sequences. Three-dimensional antibody models are commonly available and are familiar to those skilled in the art. Software programs can be used to illustrate and display probable three-dimensional conformational structures of selected candidate antibodies. These displays can be analyzed to identify the likely roles of the residues in the functioning of the candidate antibody sequences. In this way, framework residues can be selected and combined from the recipient and import sequences so that the desired antibody characteristic, such as increased affinity for the target epitope is achieved. In general, the CDRs are involved in influencing antigen binding.

Various forms of the humanized tau antibody are contemplated. For example, the humanized tau antibody may be an antibody fragment, such as a Fab, which is optionally conjugated with one or more agents to generate an immunoconjugate. Alternatively, the humanized tau antibody may be an intact antibody, such as an intact IgG1 antibody.

Human Antibodies

Alternatively, human tau antibodies can be generated. For example, transgenic animals (e.g., mice) can be produced that are capable, upon immunization, of producing a full repertoire of human antibodies in the absence of endogenous antibody production. The homozygous deletion of the antibody heavy-chain joining region ($J_H$) gene in chimeric and germ-line mutant mice results in complete inhibition of endogenous antibody production. Transfer of the human germ-line antibody gene array in such germ-line mutant mice results in the production of human antibodies upon immunization with an epitope. Methods of producing and using such genetically engineered mice to produce human antibodies are known in the art and such embodiments are within the purview of the disclosure.

Alternatively, phage display technology can be used to produce human tau antibodies and antibody fragments thereof in vitro, from antibody variable (V) domain gene repertoires from unimmunized donors. Phage display technology is known in the art and described by, for example, McCafferty et al., Nature 348:552-553 (1990); Hoogenboom and Winter, J. Mol. Biol. 227: 381 (1991).

In other embodiments, ribosome display technology can be used to produce human tau antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Plucktthun (2004) J. Immunological Methods 290:51-67).

The techniques of Cole et al., and Boerner et al., are also available for the preparation of human tau monoclonal antibodies (Cole et al., Monoclonal Antibodies and Cancer Therapy, Alan R. Liss, p. 77 (1985) and Boerner et al., J. Immunol. 147(1): 86-95 (1991). Similarly, human tau antibodies can be made by introducing human antibody loci into transgenic animals, e.g., mice in which the endogenous antibody genes have been partially or completely inactivated. Upon challenge, human antibody production is observed, which closely resembles that seen in humans in all respects, including gene rearrangement, assembly and antibody repertoire. Certain such techniques are described, for example, in U.S. Pat. Nos. 5,545,807; 5,545,806, 5,569,825, 5,625,126, 5,633,425, 5,661,016 and in the following publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995).

Finally, human tau antibodies may also be generated in vitro by activated B-cells (see U.S. Pat. Nos. 5,567,610 and 5,229,275).

Intrabodies

Intracellular antibodies (intrabodies) are recombinant antibody fragments that bind to target proteins expressed inside of the same living cell producing the antibodies. Methods of producing and using intrabodies are known in the art (see, for example, Marschall et al., mAbs, 2015, 7(6):2020-1035, which is hereby incorporated by reference in its entirety).

Antibody Fragments

Using tau antibody fragments, rather than whole tau antibodies, provides certain advantages, such as rapid clearance attributable to small sizes. Various techniques can be used for producing antibody fragments. The fragments can be derived by proteolytic digestion of intact antibodies (see, e.g., Morimoto et al., J. Biochem. Biophys. Method. 24:107-117 (1992); and Brennan et al., Science 229:81 (1985)). Alternatively, the fragments can be produced by recombinant host-cells, for example, using nucleic acids encoding fragments of tau antibodies of the present disclosure. Fab, Fv and scFv antibody fragments can all be expressed in and secreted from *E. coli*, thus allowing the straightforward production of large amounts of these fragments. Fragments of tau antibodies can also be isolated from the antibody phage libraries as discussed above. Alternatively, Fab'-SH fragments can be directly recovered from *E. coli* and chemically coupled to form F(ab')$_2$ fragments (Carter et al., Bio/Technology 10:163-167 (1992)). F(ab')$_2$ fragments can also be isolated from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The tau antibody fragment may also be a "linear antibody", e.g., as described in U.S. Pat. No. 5,641,870. Such linear antibody fragments may be monospecific or bispecific.

Effector Function Engineering

It may also be desirable to modify the tau antibodies of the present disclosure to modify effector function and/or to increase serum half-life of the antibody. For example, the Fc receptor binding site on the constant region may be modified or mutated to remove or reduce binding affinity to certain Fc receptors, such as FcgRI, FcgRII, and/or FcgRIII. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in PCT WO 99/58572 and Armour et al., Molecular Immunology 40: 585-593 (2003); Reddy et al., J. Immunology 164:1925-1933 (2000).

The constant region of the tau antibodies described herein may also be modified to impair complement activation. For example, complement activation of IgG antibodies following binding of the C1 component of complement may be reduced by mutating amino acid residues in the constant region in a C1 binding motif (e.g., C1q binding motif). Ala mutation for each of D270, K322, P329, P331 of human IgG1 significantly reduced the ability of the antibody to activate complement. For murine IgG2b, C1q binding motif constitutes residues E318, K320, and K322. Idusogie et al. (2000) J. Immunology 164:4178-4184; Duncan et al. (1988) Nature 322: 738-740. As the C1s binding motif E318, K320, and K322 identified for murine IgG2b is believed to be common for other antibody isotypes (Duncan et al. (1988) Nature 322:738-740), C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also possible to use such polar non-ionic residues as Ser, Thr, Cys, and Met in place of residues 320 and 322, but not 318, to abolish C1s binding activity. In addition, removal of carbohydrate modifications of the Fc region necessary for complement binding can prevent complement activation Glycosylation of a conserved asparagine (Asn-297) on the CH2 domain of IgG heavy chains is essential for antibody effector functions (Jefferis et al. (1998) Immunol Rev 163:59-76). Modification of the Fc glycan alters IgG conformation and reduces the Fc affinity for binding of complement protein C1q and effector cell receptor FcR (Alhorn et al. (2008) PLos ONE 2008; 3:e1413). Complete removal of the Fc glycan abolishes CDC and ADCC. Deglycosylation can be performed using glycosidase enzymes for example Endoglycosidase S (EndoS), 108 kDa enzyme encoded by the gene endoS of *Streptococcus pyogenes* that selectively digests asparagine-linked glycans on the heavy chain of all IgG subclasses, without action on other antibody classes or other glycoproteins (Collin et al. (2001) EMBO J 2001; 20:3046-3055).

To increase the serum half-life of the antibody, a salvage receptor binding epitope can be incorporated into the antibody (especially an antibody fragment) as described in U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Tau antibodies of the present disclosure, or antibody fragments thereof, can be further modified to contain additional non-proteinaceous moieties that are known in the art and readily available. In some embodiments, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in Remington: The Science and Practice of Pharmacy, 20th Ed., Alfonso Gennaro, Ed., Philadelphia College of Pharmacy and Science (2000).

In further embodiments, tau antibodies or antigen binding fragments thereof can be conjugated to a label, for example, an enzyme label, a radioisotope label, a fluorescent label, or a bioluminescent label. The labels are typically used for detection and visualization of antigen-antibody complex. Non-limiting examples of the enzyme labels are horseradish peroxidase label, alkaline phosphatase, β-galactosidase, luciferase, acetylcholine esterase, and glucose oxidase. Additional examples of enzymes appropriate for labeling antibodies for detection and visualization of antigen-antibody complex are well known to a person of ordinary skill in the art and such embodiments are within the purview of the current disclosure. Non-limiting examples of radioisotope labels are $^{125}I$, $^{35}S$, $^{14}C$, $^{32}P$ and $^{3}H$. Additional examples of radiolabels appropriate for labeling antibodies for detection and visualization of antigen-antibody complex are well known to a person of ordinary skill in the art and such embodiments are within the purview of the current disclosure. Non-limiting examples of fluorescent labels are umbelliferone, fluorescein, rhodamine, dichlorotriazinylamine fluorescein, dansyl chloride, fluorescein isothiocyante (FITC), phycoerythrin (PE), Cy5-phycoerythrin (Cy5-PE), Cy7-phycoerythrin (Cy7-PE), allophycocyanin (APC), Cy7-allophycocyanin (Cy7-APC), texas red (TR) and cascade blue. Additional examples of fluorescent labels appropriate for labeling antibodies for detection and visualization of antigen-antibody complex are well known to a person of ordinary skill in the art and such embodiments are within the purview of the current disclosure. Non-limiting examples of bioluminescent labels are photoprotein aequorin, adenosine triphosphate, nicotinamide adenine dinucleotide and D-luciferin. Additional examples of bioluminescent labels appropriate for labeling antibodies for detection and visualization of antigen-antibody complex are well known to a person of ordinary skill in the art and such embodiments are within the purview of the current disclosure.

A further embodiment of the disclosure also provides a kit comprising an antibody or antigen binding fragment thereof. The kit can contain the antibody along with additional reagents required for processing of a sample for the immunoassay, reagents for conducting the immunoassay and instructional materials and manuals for performing the immunoassay.

As noted above, the tau antibodies and the antigen binding fragments thereof disclosed herein could be used for treating or preventing tauopathies. Accordingly, certain embodiments of the disclosure provide methods of treating or preventing a tauopathy in a subject, comprising administering to the subject a therapeutically effective amount of tau antibodies or the antigen binding fragments thereof disclosed herein. Non-limiting examples of tauopathies that can be treated according to the methods of the disclosure include AD, chronic traumatic encephalopathy, corticobasal degeneration, frontotemporal labor degeneration, Pick disease, or progressive supranuclear palsy.

Tau antibodies and the antigen binding fragments thereof disclosed herein when used for treating or preventing tauopathies are administered to subjects in the form of pharmaceutical compositions. Accordingly, certain embodiments of the disclosure provide pharmaceutical compositions comprising tau antibodies or antigen binding fragments thereof.

Tau antibodies and the antigen binding fragments thereof disclosed herein also have diagnostic utility. Therefore methods of using the antibodies or antigen binding fragments thereof for diagnostic purposes as the detection of tau in a subject or in tissue samples derived from a subject. In some embodiments, the subject is a human. In some embodiments, the subject is suffering from a neurodegenerative disorder, particularly, a tauopathy, such as AD, chronic traumatic encephalopathy, corticobasal degeneration, frontotemporal labor degeneration, Pick disease, progressive supranuclear palsy, and Parkinsonism linked to chromosome 17 with tau pathology.

The diagnostic methods of the disclosure involve administering tau antibodies or antigen binding fragments thereof to a subject and detecting the antibodies or antigen binding fragments thereof bound to tau protein in the subject. Binding of the tau antibodies or antigen binding fragments thereof may be quantified, for example, by non-invasive techniques such as positron emission tomography (PET), X-ray computed tomography, single-photon emission computed tomography (SPECT), computed tomography (CT), and computed axial tomography (CAT). In some embodiments, the tau antibodies or antigen binding fragments thereof are conjugated to a label suitable for an in vivo visualization and the binding of the tau antibodies or antigen binding fragments to tau protein in a subject is visualized using the detectable label. Some of the labels discussed above in connection with the labels conjugated to tau antibodies or antigen binding fragments thereof can be used in such embodiments.

In some embodiments, the diagnostic methods involve detecting tau in biological samples, such as biopsy a specimen, a tissue, or a cell. A tau antibody or an antigen binding fragment thereof disclosed herein is contacted with the biological sample and tau-bound antibody or antigen binding fragment thereof is detected. The detection method may involve quantification of the tau-bound antibody. Antibody detection in biological samples can be performed with any methods known in the art, including immunofluorescence microscopy, immunocytochemistry, immunohistochemistry, ELISA, FACS analysis or immunoprecipitation.

Further embodiments of the disclosure provide methods of producing the tau antibodies or antigen binding fragments thereof as disclosed herein. Typically, a nucleotide sequence encoding a tau antibody or an antigen binding fragment thereof is incorporatged into a vector. Such vector is introduced into a host cell and the host cell is cultured under conditions that are appropriate for the expression, preferably, a high level expression, of the tau antibody or the antigen binding fragment thereof encoded by the vector.

Vectors useful in the methods of the disclosure include plasmids, viral vectors, yeast articficla chromosomes, and cosmids. Additional vectors are known in the art and such embodiments are within the purview of the disclosure.

Typical host cells include bacteria, such as *E. coli*, fungi, preferably, yeast such as *Saccharomyces cerevisiae*, and eukaryotic cell culture systems, preferably, mammalian cell culture systems. Additional host cells are known in the art and such embodiments are within the purview of the disclosure.

Materials and Methods

Mice

Tau null (tau KO) mice and tau transgenic (Tg) mice line PS19 expressing human 1N/4R tau with the P301S mutation driven by the mouse prion promoter were obtained from Jackson Laboratory (Bar Habor, Me.). Tau Tg mice line JNPL3 expressing human 0N/4R tau with the P301L mutation were previously described.

Antibodies

AT8 (Thermo-fisher) is a mouse monoclonal antibody specific towards phosphorylation sites S202 and T205 in tau but that can be influenced by phosphorylation at S199 or S208. PHF1 is a mouse monoclonal antibody specific towards phosphorylation sites S396 and S404 in tau. Rabbit polyclonal antibody (H-150) raised against the first 150 amino acids of human tau was obtained from Santa Cruz Biotechnologies (Dallas, Tex.), and rabbit polyclonal antibodies 3026 and 3029 raised against recombinant full-length 0N/3R tau was generated by GenScript USA Inc. (Piscataway, N.J.).

Generation of New Mouse Tau Monoclonal Antibodies

Phosphopeptides EIVYKpSPVVSGDTpSPRHLS (p391-409, SEQ ID NO: 3) and DRSGYSpSPGpSPGpTPGSRSR (p193-211, SEQ ID NO: 4) corresponding, respectively, to residues 391-409 and 193-211 in the 2N/4R human tau isoform (SEQ ID NO: 1), with a C residue added at the carboxy-termini for chemical conjugation were synthesized and purified by GenScript USA Inc. (Piscataway, N.J.). Lyophilized peptides were reconstituted in phosphate buffered saline (PBS) and conjugated to Imject maleimide-activated mariculture keyhole limpet hemocyanin (mcKLH; Thermo Scientific, Waltham, Mass.). 2-3 month old female BALB/c mice (Jackson Laboratory, Bar Harbor, Me.) were used for immunization. Injection solutions were emulsified by vortexing for 15 minutes were prepared by combining 100 μg KLH-conjugated peptide in 200 μl PBS with 100 μl of Freund's complete adjuvant (Sigma Aldrich, St. Louis, Mo.) for the initial subcutaneous injection. Three weeks following the initial injection, mice were boosted with an intraperitoneal (IP) injection of 50 μg KLH-conjugated peptide in 200 μl PBS emulsified with 100 μl of Freund's incomplete adjuvant (Sigma Aldrich, St. Louis, Mo.). Three weeks later, mice were boosted with an IP injection of 50 μg KLH-conjugated peptide in PBS. Three days later, mice were euthanized and spleens were harvested using aseptic technique.

Mouse myeloma (Sp2/O-Ag14; ATCC, Manassas, Va.) cells were maintained in high glucose (4.5 gm/L) Dulbecco's Modified Eagle Medium (DMEM) with 10% NCTC 135 Media (Sigma Aldrich, St. Louis, Mo.), 20% hybridoma grade fetal bovine serum (FBS; Hyclone, Logan, Utah), 100 U/ml penicillin, 100 U/ml streptomycin, 2 mM L-glutamine, 0.45 mM pyruvate, 1 mM oxaloacetate, and 0.2 U/ml insulin at 37° C. and 8% $CO_2$. Spleens were gently homogenized in 5% FBS/Hank's balanced salt solution (HBSS; Lonza, Walkersville, Md.) and centrifuged to pellet cells. The cell pellet was resuspended in red blood cell lysis buffer for one minute (Sigma Aldrich, St. Louis, Mo.) and diluted with HBSS. The cells were then washed twice by centrifuging at 100 g for 10 minutes and resuspended in HBSS. Sp2/O-Ag14 cells were also washed twice with HBSS. Five million Sp2/O-Ag14 cells were added to 50 million spleen cells, and after centrifuging at 100 g for 10 minutes onto a culture dish, fusion was induced with 50% polyethylene glycol 1450 (Sigma Aldrich, St. Louis, Mo.). After washing with HBSS, cells were incubated in Sp2/O-Ag14 media at 37° C. with 8% $CO_2$ overnight. The next day, the cells were gently detached from the plate and distributed into 96 well plates with Sp2/O-Ag14 media/0.5% hybridoma enhancing supplement (Sigma Aldrich, St. Louis, Mo.)/HAT selection supplement (Sigma Aldrich, St. Louis, Mo.).

Hybridoma Screening

All hybridoma clones were screened for reactivity to the respective unconjugated peptide that was used for immunization by enzyme-linked immunosorbent assay (ELISA). MaxiSorp plates (Thermo Scientific, Waltham, Mass.) were coated with 1 μg/ml peptide in PBS and blocked with 5% FBS/PBS. Media from the hybridomas was applied to plates, which were then incubated at room temperature. Next, the plates were washed with PBS and incubated with goat anti-mouse secondary antibody conjugated to horseradish peroxidase (HRP; Jackson Immuno Research Labs, West Grove, Pa.) at room temperature. Then, plates were washed and TMB substrates (Pierce, Rockford, Ill.) were applied until color changes were observed. Reactions were then quenched with 1 M HCl and absorbance was measured at 450 nm. Clones that were positive by ELISA were transferred to larger culture plates as needed. The positive clones were next screened by immunohistochemistry of a human AD autopsy case with abundant tau pathology.

Antibody clones were isotyped with the mouse monoclonal antibody isotyping kit purchased from Sigma-Aldrich (St. Louis, Mo.).

Immunohistochemistry Analyses

Paraffin embedded, formalin fixed human brain tissue was obtained. Sequential tissue sections were deparaffinized with xylenes and sequentially rehydrated with graded ethanol solutions (100-70%). Antigen retrieval was performed by incubating sections in 0.05% Tween-20 in a steam bath for 60 minutes. Endogenous peroxidase activity was quenched with 1.5% hydrogen peroxide/0.005% Triton-X-100/PBS for 20 minutes. Following washes, sections were blocked with 2% FBS/0.1 M Tris, pH 7.6 and incubated with primary antibody overnight at 4° C. Following washing with 0.1 M Tris, pH 7.6, sections were incubated with biotinylated horse anti-mouse IgG secondary antibody (Vector Laboratories, Burlingame, Calif.) diluted in 2% FBS/0.1 M Tris pH 7.6 for 1 hour. Next, sections were washed with 0.1 M Tris, pH 7.6, then incubated with streptavidin-conjugated HRP (VECTASTAIN ABC kit; Vector Laboratories, Burlingame, Calif.) diluted in 2% FBS/0.1 M Tris pH 7.6 for 1 hour. Sections were washed with 0.1 M Tris, pH 7.6, and then developed with 3,3'-diaminobenzidine (DAB kit; KPL, Gaithersburg, Md.). Reactions were stopped by immersing the slides in 0.1 M Tris, pH 7.6, and sections were counterstained with Mayers hematoxylin (Sigma Aldrich, St. Louis, Mo.). Next, sections were dehydrated with an ascending series of ethanol solutions (70%-100%) followed by xylenes and coverslipped using cytoseal (Thermo Scientific, Waltham, Mass.).

Recombinant Tau Protein Production and Purification

Human full-length tau cDNA (0N/3R or 2N/4R isoform) cloned into the bacterial expression vector pRK172 was obtained. pRK172 plasmid expressing human 0N/3R tau with the S199A, T202A or T205A mutations (numbered according to the 2N/4R tau isoform) or human 2N/4R tau with the S396A or S404A mutations (numbered according to the 2N/4R tau isoform) was created with oligonucleotides corresponding to the amino acid substitutions by QuickChange site-directed mutagenesis (Stratagene, La Jolla, Calif.). These recombinant tau proteins were expressed in *E. coli* BL21 and purified.

Kinase Reactions

Tau proteins (0.2 mg/ml) were phosphorylated with either glycogen synthase kinase 3β (GSK3β; 2.5 U/μl; New England Biolabs, Ipswich, Mass.) or p42 mitogen-activated protein kinase (MAPK; 0.5 U/μl; New England Biolabs, Ipswich, Mass.) in 50 mM Tris, pH 7.5, 10 mM $MgCl_2$, 0.1 mM EDTA, 2 mM DTT, 0.1% Brij 35, ATP 200 μM for 2 hours at 30° C. followed by heat inactivation at 95° C. for 5 minutes. Samples were diluted in SDS-sample buffer and 100 ng of each tau protein was loaded on a separate lane on SDS-polyacrylamide gels for immunoblot analysis.

Preparation of Total Mouse Brain Protein Lysates

Tau KO, PS19 Tg or non-transgenic (nTg) mice were euthanized and the brains were harvested. Brain tissue was lysed with 2% SDS/50 mM Tris, pH 7.5 using a probe sonicator until homogenous and incubated for 10 minutes at 100° C. Protein concentrations were determined by bicinchoninic acid (BCA) assay (Thermo Scientific) using bovine serum albumin (BSA) as the standard. SDS sample buffer was added, and equal amounts of protein (40 µg) were resolved by SDS-PAGE and analyzed by immunoblot.

Preparation of Sarkosyl-Insoluble Human Temporal Cortex Samples

Frozen human brain tissue was obtained. Pulverized temporal cortex tissue from human AD cases (n=3) or control (n=2) was homogenized in 3 ml of high-salt (HS) buffer (50 mM Tris-HCl pH 7.5, 0.75 M NaCl, 2 mM EDTA, 50 mM NaF with a cocktail of protease inhibitors) per gram of tissue and sedimented at 100,000 g for 30 minutes at 4° C. Supernatants were collected (HS fraction) and pellets were re-suspended in 2 ml of HS buffer containing 1% Triton X-100 per gram of tissue. Samples were sedimented at 100,000 g for 30 minutes at 4° C. and the supernatants were collected (HS/Triton-soluble fraction). Pellets were re-extracted in HS buffer/1% Triton X-100. Samples were sedimented at 100,000 g for 30 min at 4° C. and supernatants were discarded. Pellets were re-suspended in 1 ml of HS buffer containing 1% sarkosyl per gram of tissue, incubated at 37° C. for 30 min, and sedimented at 100,000 g for 30 minutes at 4° C. Supernatants were collected (sarkosyl-soluble fraction). The detergent-insoluble pellets were extracted in 0.5 ml of 4 M urea, 2% SDS, 25 mM Tris-HCl pH 7.6 per gram of tissue, sonicated, and sedimented at 100,000 g for 30 min at 25° C. Protein concentrations were determined by BCA assay (Thermo Scientific) using bovine serum albumin (BSA) as the standard. SDS sample buffer was added, and equal amounts of protein (10 µg) were resolved by SDS-PAGE and analyzed by immunoblot.

Immunoblotting Analyses

Protein samples were resolved by electrophoresis on 10% polyacrylamide gels, then electrophoretically transferred to nitrocellulose membranes. Membranes were blocked with 5% milk/Tris-buffered saline (TBS) and then incubated overnight at 4° C. with primary antibodies diluted in 5% BSA/TBS. Following washing, blots were incubated with HRP conjugated goat anti-mouse IgG/IgM (heavy and light chains, but pre-absorbed to human, bovine and horse serum proteins) or goat anti-rabbit secondary antibodies (Jackson Immuno Research Labs, West Grove, Pa.) diluted in 5% milk/TBS for 1 hour. Following washing, protein bands were visualized using Western Lightning-Plus ECL reagents (PerkinElmer, Waltham, Mass.), and images were captured using the GeneGnome XRQ system and GeneTools software (Syngene, Frederick, Md.).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the disclosure. These examples should not be construed as limiting. All percentages are by weight and all solvent mixture proportions are by volume unless otherwise noted.

EXAMPLES

Example 1: Generation and Characterization of Anti-Phospho Antibodies Targeted to S396/S404 in Tau To generate antibodies similar to the PHF1 epitope, mice were immunized with the synthetic phosphopeptide EIVYKpSPVVSGDTpSPRHLS (SEQ ID NO: 3) corresponding to residues 391-409 in 2N/4R human tau and containing phosphorylated S396 and S404. Several hybridomas, termed the PHF series, were identified by ELISA screening as well as initial screening for reactivity of tau pathology by immunohistochemistry of a human AD autopsy case with abundant tau pathology. Five hybridomas (PHF2, PHF15, PHF17, PHF20 and PHF22) were identified using these criteria. To determine the specificity of these monoclonal antibodies, full-length WT, S396A and S404A 2N/4R human tau were in vitro phosphorylated with known tau kinases (p42 MAPK or GSK3β) and used these tau proteins for immunoblotting analysis (FIG. 1). Previously characterized antibody PHF1, which recognizes tau phosphorylated at both S396 and S404 was used as a control. WT but not S396A or S404A tau phosphorylated with GSK3β reacted with PHF1 as expected. PHF20 reacted with WT or S396A but not S404A (all proteins tau phosphorylated with either GSK3β or p42 MAPK), demonstrating that this antibody preferentially recognizes tau phosphorylated at S404. Since PHF1 did not react with tau phosphorylated with p42 MAPK these data also show that p42 MAPK in vitro phosphorylated tau only at S404 and not S396. Antibodies PHF2, PHF15, PHF17 and PHF22 all revealed the same relativities as PHF1 in these assays demonstrating that they recognize tau only when phosphorylated at both S396 and S404.

The specificity of the new PHF series of antibodies was then assessed using total mouse brain lysates from tau KO, nTg and PS19 tau Tg mice (FIG. 2). Antibodies PHF2, PHF15, PHF17 and PHF 20 specifically reacted with mouse tau in nTg mice and with both mouse and human tau in lysates derived from PS19 tau Tg mice. PHF2, PHF15, and PHF 20 displayed no cross-reactivity in brain extracts from tau KO mice, but PHF17 weakly cross-reacted with a ~150 kDa non-tau protein band. PHF22 recognized mouse and human tau, but it also cross-reacted with some non-specific higher molecular mass proteins still present in lysate from tau KO mice.

Example 2: Generation and Characterization of Antibodies Targeting the Phospho-S199/S202/T205 Tau Epitope To generate antibodies similar to the AT8 epitope, mice were immunized with the synthetic phosphopeptide DRSGYSpSPGpSPGpTPGSRSR (SEQ ID NO: 4) corresponding to residues 193-211 in 2N/4R human tau with phosphorylated S199, S202 and T205. Several hybridomas were identified by ELISA screening with the corresponding unconjugated peptide followed by immunohistochemistry for tau pathology in a human AD autopsy case. Nine of these hybridomas (1H5, 2D1, 3C9, 4A10, 5F2, 6G12, 7F2, 8G5 and 10G12) were further characterized. To determine the specificity of these monoclonal antibodies, WT, S199A, S202A and T205A 0N/3R human tau (mutations numbered according to the sequence of 2N/4R human tau) were phosphorylated with p42 MAPK or GSK3β and immunoblotting analysis was performed (FIG. 3). Antibodies 6G12, 7F2, 8G5 and 10G12 reacted with tau phosphorylated with either p42 MAPK or GSK3β, but not when T205 was mutated to an A, indicating that they all recognize tau phosphorylated at T205. Antibodies 2D1, 4A10 and 5F2 reacted with phosphorylated and non-phosphorylated tau showing that their recognition epitopes are phosphorylation independent. Antibody 1H5 reacted with phosphorylated tau but could also recognize non-phosphorylated tau to a lesser degree, demonstrating that it prefers phosphorylated tau. Antibody 3C9 only recognized phosphorylated tau and prefers tau phosphorylated at T205, as shown by the reduced reactivity with phosphorylated T205A tau. However, 3C9 is a more promiscuous phospho-antibody that can also recognize tau phosphorylated at either S199 or S202 since the T205A mutation does not completely block its reactivity with phosphorylated tau.

The specificity of the antibodies generated to the AT8 epitope were then assessed using mouse brain lysates from tau KO, nTg, and PS19 tau transgenic mice (FIG. 2). All of these antibodies detected endogenous mouse tau in nTg mice and both mouse and human tau in PS19 Tg mice, and they were quite specific for tau, as demonstrated by their lack of reactivity to lysates from tau KO mice. They are much more specific than AT8, which reacted with many additional higher molecular mass protein bands present in lysates from tau KO mice (FIG. 2). The same cross-reactivity of the AT8 antibody with non-tau proteins was observed in three independent lots of the AT8 antibody.

Figure 4:
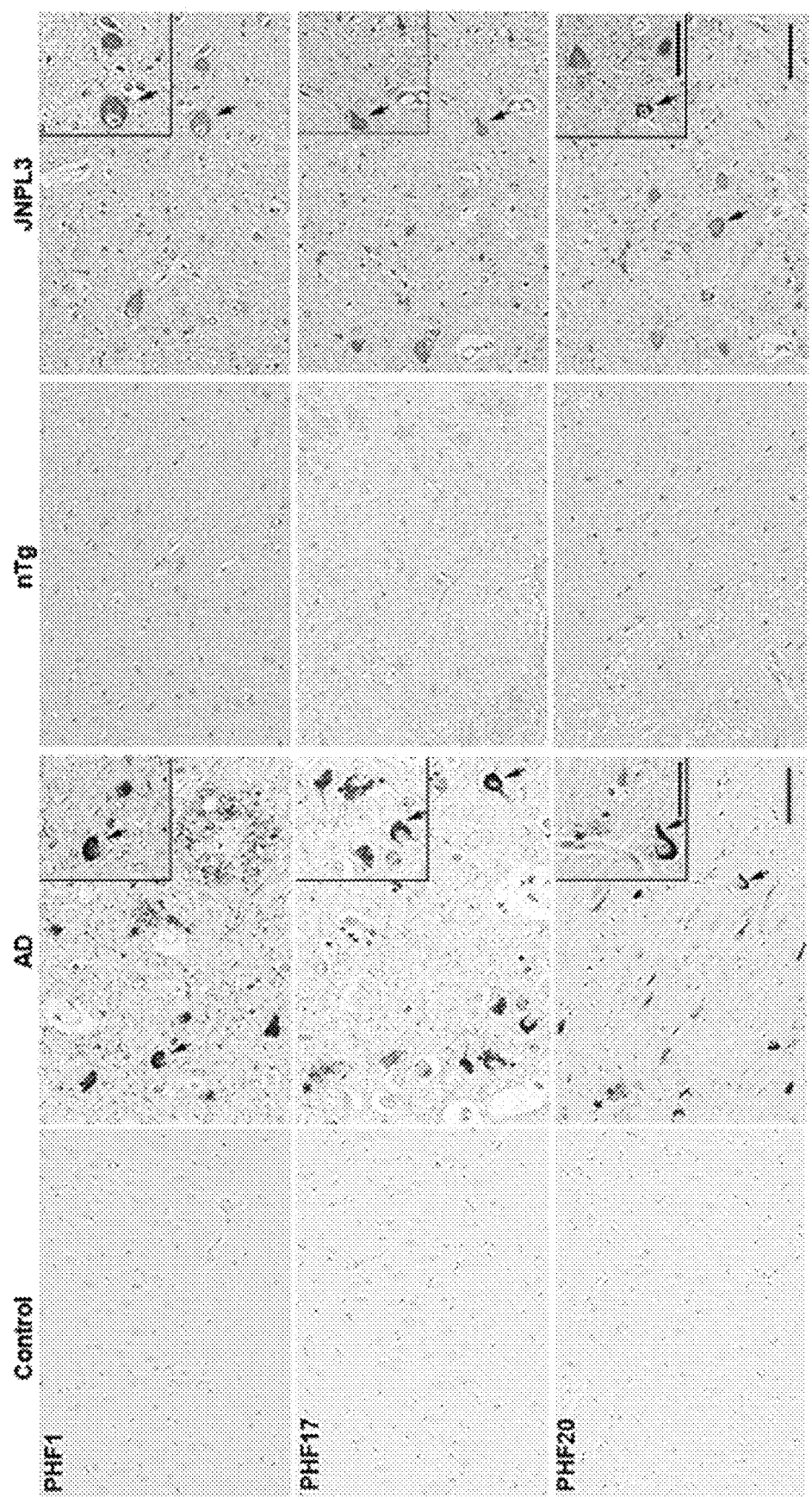
FIG. 4 shows immunocytochemistry of representative tau pathology in human AD brain and JNPL3 Tg mice with antibodies PHF17 and PHF20. Immuno-reactivity of previously characterized phospho-tau antibodies PHF1 and new tau antibodies PHF17 or PHF20 in the hippocampus of a control subject or a subject with AD, and in the spinal cord of 12 month old nTg and JNPL3 Tg mice. Arrows indicate NFTs in human brain or NFT-like inclusion pathology in JNPL3 mice. Asterisks depict dystrophic neurites within senile plaques. Bar=100 μm, and 200 μm for insets.
Figure 5:
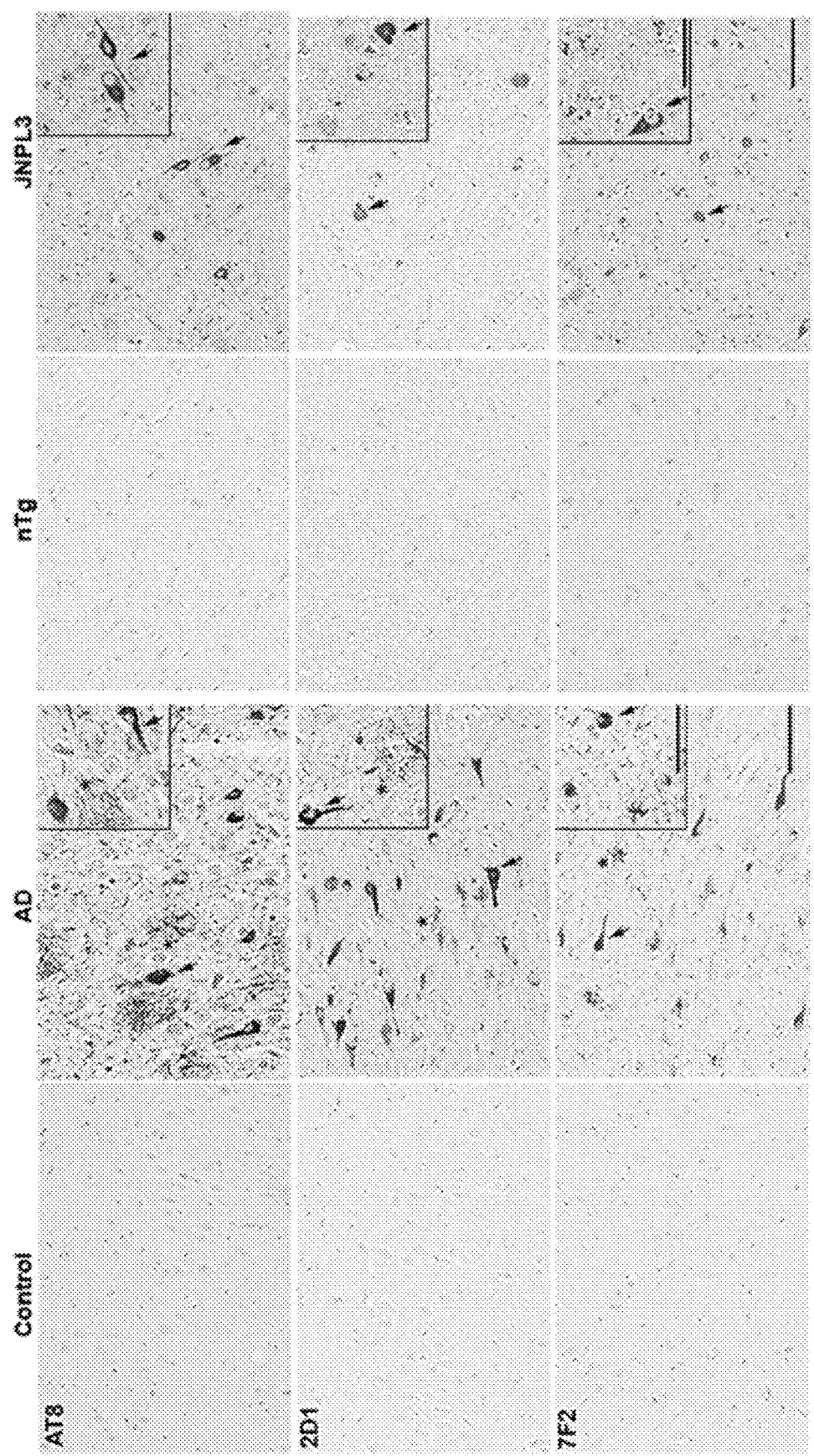
FIG. 5 shows immunocytochemistry of representative tau pathology in human AD brain and JNPL3 Tg mice with antibodies 2D1 and 7F2. Immuno-reactivity of previously characterized phospho-tau antibodies AT8 and new tau antibodies 2D1 or 7F2 in the hippocampus of a control subject or a subject with AD, and in the spinal cord of 12 month old nTg and JNPL3 Tg mice. Arrows indicating NFTs in human brain or NFT-like inclusion pathology in JNPL3 mice. Asterisks depict dystrophic neurites within senile plaques. Bar=100 μm, and 200 μm for insets.
Figures 6A, 6B, 6C, 6D, 6E:
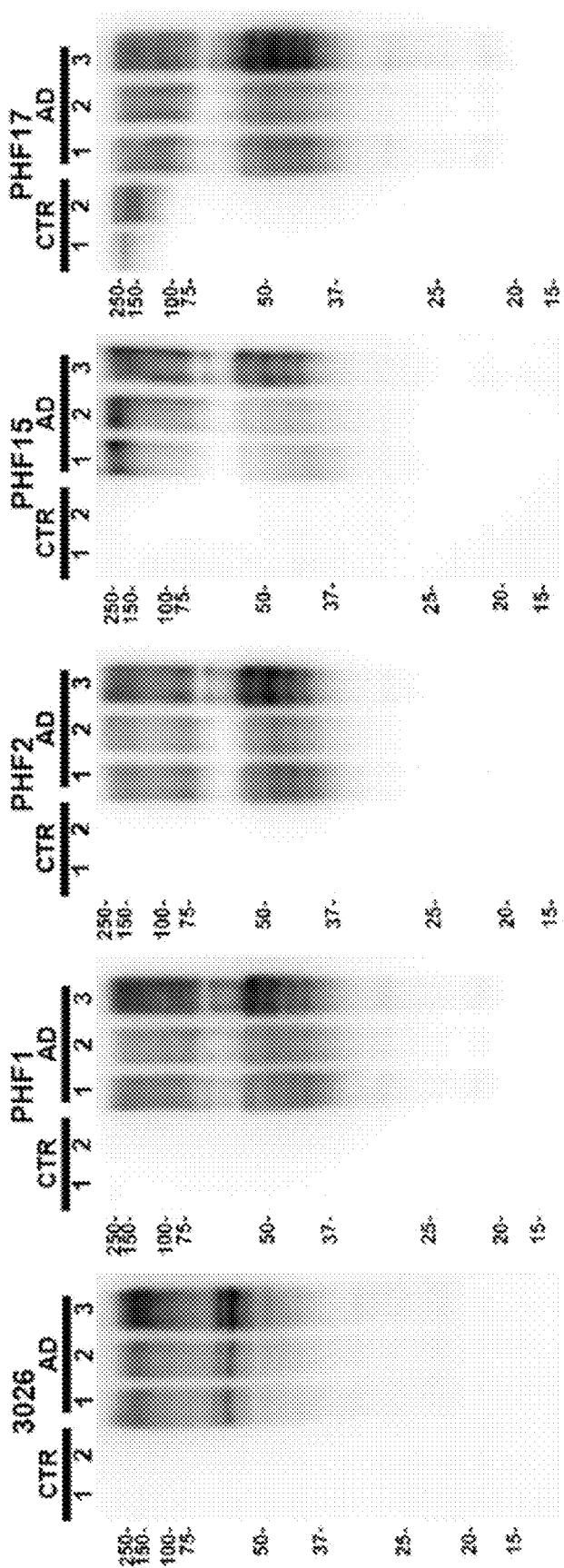
FIGS. 6A to 6Q show characterization of the tau antibodies 3026 (FIG. 6A), PHF1 (FIG. 6B), PHF2 (FIG. 6C), PHF15 (FIG. 6D), PHF17 (FIG. 6E), PHF20 (FIG. 6F), PHF22 (FIG. 6G), AT8 (FIG. 6H), 1H5 (FIG. 6I), 2D1 (FIG. 6J), 3C9 (FIG. 6K), 4A10 (FIG. 6L), 5F2 (FIG. 6M), 6G12 (FIG. 6N), 7F2 (FIG. 6O), 8G5 (FIG. 6P), and 10G12 (FIG. 6Q) in detecting biochemically sarkosyl-insoluble tau in human brain lysates from AD patients. Immunoblotting analysis of the sarkosyl-insoluble fraction from the temporal cortex of human AD cases (n=3) and control cases (CTR; n=2). Samples were biochemically fractionated as described in "Material and Methods". Equal amounts of proteins (10 μg) from each sample was resolved onto 10% polyacrylamide gels and analyzed by immunoblotting with each antibody indicated above blot, including total tau antibody 3026. The mobilities of molecular mass markers are shown on the left.
Figures 6F, 6G, 6H, 6I, 6J:
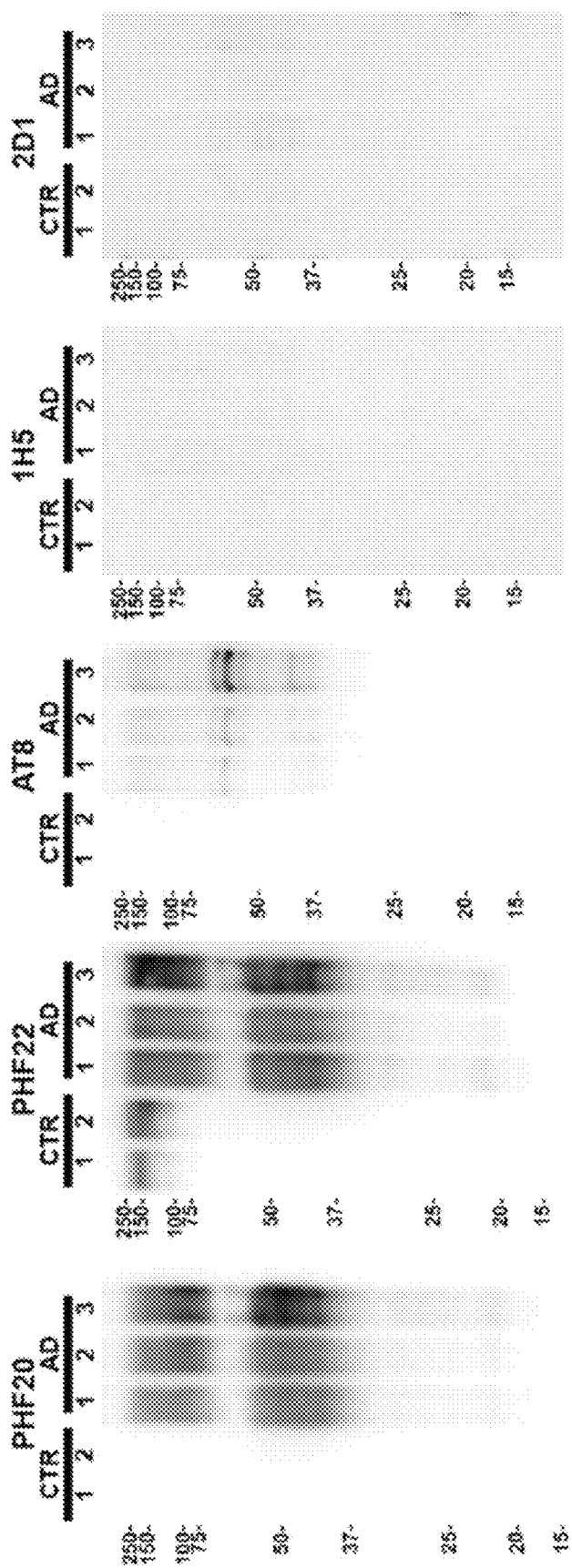
Figures 6K, 6L, 6M, 6N, 6O:
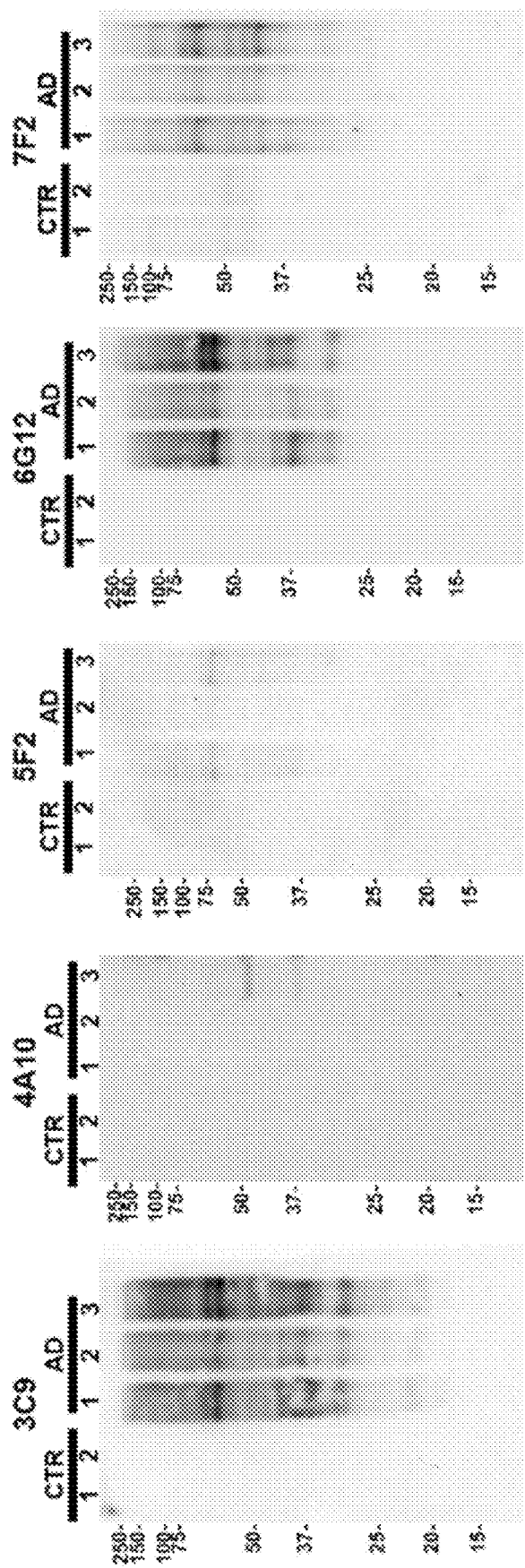
Figures 6P, 6Q:
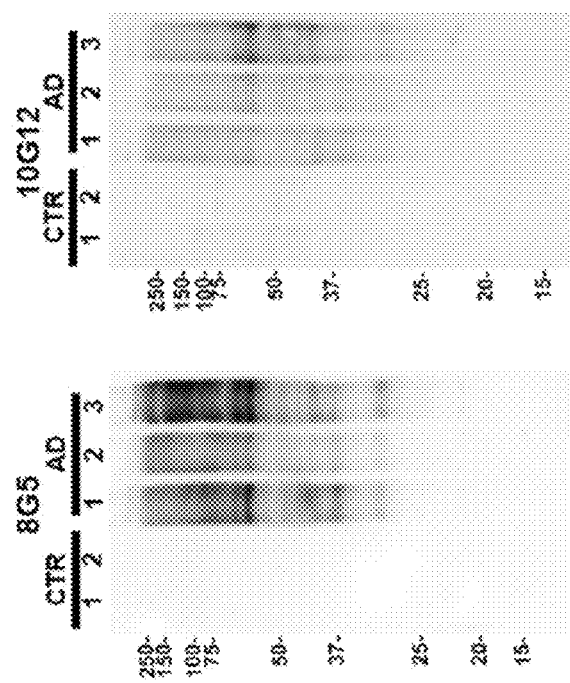

All of the new tau antibodies were compared for immunoreactivity of tau pathology using brain tissue from AD and control patients. All of these antibodies reacted with NFTs, but antibodies PHF17, PHF20, PHF22, 2D1 and 7F2 yielded the strongest staining with little background (FIG. 4; data not shown); however, as shown in the immunoblotting screen, PHF22 is not completely tau specific (FIG. 2). Antibodies 2D1 and 7F2 also provided strong detection of neuropil threads in addition to senile plaque dystrophic neurites. Antibodies PHF17, PHF20, 2D1 and 7F2 were also tested for immunoreactivity of tau pathology in the JNPL3 Tg mouse model, where they showed strong immunoreactivity (FIGS. 4 and 5).

The ability of the new monoclonal antibodies to detect sarkosyl-insoluble tau in the temporal cortex tissue from AD (n=3) versus control (n=2) cases was also assessed by immunoblotting (FIG. 6). Of the new PHF antibodies, PHF2, PHF15 and PHF20 specifically detect detergent insoluble tau only in the AD cases, while PHF17 and PHF22 showed some non-specificity in the control lanes, consistent with the immunoblot results from the mouse total brain lysates. The phospho-specific antibodies (3C9, 6G12, 7F2, 8G5, 10G12) generated to the AT8 epitope showed higher levels of detection of sarkosyl-insoluble tau in AD samples than our phospho-independent or phospho-selective antibodies (1H5, 2D1, 4A10, 5F2).

Example 3: Superior Characteristics of the Monoclonal Antibodies Against Phosphorylated Tau Previous studies have demonstrated that tau phosphorylation at the AT8 and PHF1 epitopes occur early in disease and that these can be targets for immunotherapy. New monoclonal antibodies having similar epitopes to these epitopes are generated. The specificity for tau and reactivity for pathological inclusions of these antibodies were validated. Lysates from tau KO mice as controls were used in the analysis to establish the level of specificity and cross-reactivity of the antibodies with other proteins in the brain homogenates. The apparent non-specificity of tau antibodies can typically arise from two main sources. First, because of the low amounts of phosphorylated tau present in a normal wild type mouse, anti-phospho-tau antibodies can show increased non-specific cross-reactivity. This can probably explain the significant cross-reactivity of the original AT8 clone to multiple high molecular weight species shown here, present in both nTg and tau KO mice. None of the antibodies within our newly generated series, except for PHF 17 and PHF22, show detectable cross-reactivity with non-tau species. A second reported source of erroneous tau detection can arise from the presence of mouse Ig in the brain homogenates. This apparent non-specificity of anti-tau antibodies in mouse homogenates can be due to the reactivity of the secondary anti-mouse IgG used for detection with endogenous Ig, which is approximately the same molecular mass as tau. None of the mice included in the studies describes in these Examples were perfused before harvesting brains. Despite, mouse Ig reactivity was not observed for the monoclonal antibodies disclosed herein.

All of the newly characterized tau antibodies recognize both endogenous mouse tau as well as human 1N/4R tau present in PS19 Tg mice. By immunoblotting analysis, the human tau expressed in PS19 mice migrates slower (i.e. has an apparent larger molecular mass) than endogenous tau in nTg because these transgenic mice express the 1N/4R human tau isoform, while 0N/4R tau is the predominant isoform expressed in adult mouse brain.

The screen for epitope specificity showed that PHF20 is specific for tau phosphorylated at S404, while other new PHF antibodies (PHF2, PHF15, PHF17 and PHF 22; Table 1) are similar to PHF1, recognizing tau phosphorylation at both S396 and S404. All these antibodies show strong reactivity with tau in the sarkosyl-insoluble fractions of human AD temporal cortex, while PHF2, PHF15, and PHF20 show no cross-reactivity in the control samples. These antibodies can be used to compare the progressive pathological phosphorylation of one versus both of these phosphorylation sites.

All of the antibodies generated in attempt to mimic the AT8 epitope were shown by immunoblotting to be relatively specific for tau and even more specific than the AT8 antibody. One set of antibodies is specific for phosphorylated T205, while another group is relatively phosphorylation independent (Table 1). In particular, one of these antibodies, clone 7F2, binds tau pathology in human tissue and is specific for tau phosphorylated at T205. While another antibody, clone 2D1, is phosphorylation-independent, reacting with both phosphorylated and non-phosphorylated tau. However, all of new phospho-specific antibodies (3C9, 6G12, 7F2, 8G5, 10G12) generated against the AT8-like epitope showed robust detection of tau in the sarkosyl-insoluble samples of AD human brain tissue, while the phospho-independent antibodies (1H5, 2D1, 4A10, 5F2) displayed much weaker signal. In addition, the comparison of the sarkosyl-insoluble tau profiles detected by immunoblotting with the PHF antibodies relative to the phospho-specific antibodies raised against the AT8 epitope revealed marked differences. Immunoblotting patterns among the antibodies directed to the same epitope, however, were more conserved. These differences could be due to altered tau species with altered phosphorylation and/or conformational properties or additional types of post-translational modifications such as a cross-linking and cleavage. Nevertheless, these data demonstrate the diverse nature of aggregated tau species even within the same brain samples.

Tauopathies can progress by inter-cellular transmission prionoid mechanisms and can be secreted in a diseased brain. Consequently, tau immunotherapies have been successful in mitigating or halting tauopathy in preclinical models. Indeed, one such humanized antibody (ABBV-8E12) has been approved to proceed to Phase 2 clinical trial in early AD and progressive supranuclear palsy patients (Clinical Trial #NCT02880956 and #NCT02985879).

Given the enormous therapeutic promise for tau antibodies in patients and because tauopathies are a wide spectrum of diseases, tau immunotherapies may have to be tailored at different disease stages or in different tauopathy patients with antibodies that have avidity to progression-specific phosphorylation epitopes, disease-specific conformations, or even different antibody effector functions. Certain embodiments of the disclosure provide a series of new monoclonal antibodies recognizing tau phosphorylated at S396/S404, S404 or T205 and several new phosphorylation independent monoclonal antibodies against amino acid residues 193-211 in human tau. Accordingly, each of the antibodies described herein or combinations thereof, having phospho-independent or phospho-specific tau epitopes at different phosphorylation sites, can be used in robust therapeutic regimen.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any disclosure or embodiment thereof disclosed herein can be combined with any and/or all other elements or limitations (individually or in any combination) or any other disclosure or embodiment thereof disclosed herein, and all such combinations are contemplated within the scope of the disclosure without limitation thereto.

REFERENCES

1. Cleveland D W, Hwo S Y, Kirschner M W. Purification of tau, a microtubule-associated protein that induces assembly of microtubules from purified tubulin. J. Mol. Biol. 1977; 116: 207-225.
2. Weingarten M D, Lockwood A H, Hwo S Y, Kirschner M W. A protein factor essential for microtubule assembly. Proc. Natl. Acad. Sci. U.S.A 1975; 72: 1858-1862.
3. Neve R L, Harris P, Kosik K S, Kurnit D M, Donlon T A. Identification of cDNA clones for the human microtubule-associated protein tau and chromosomal localization of the genes for tau and microtubule-associated protein 2. Brain Res. 1986; 387: 271-280.
4. Andreadis A, Brown W M, Kosik K S. Structure and novel exons of the human tau gene. Biochemistry 1992; 31: 10626-10633.
5. Goedert M, Spillantini M G, Potier M C, Ulrich J, Crowther R A. Cloning and sequencing of the cDNA encoding an isoform of microtubule-associated protein tau containing four tandem repeats: differential expression of tau protein mRNAs in human brain. EMBO J. 1989; 8: 393-399.
6. Goedert M, Spillantini M G, Jakes R, Rutherford D, Crowther R A. Multiple isoforms of human microtubule-associated protein tau: sequences and localization in neurofibrillary tangles of Alzheimer's disease. Neuron 1989; 3: 519-526.
7. Cleveland D W, Hwo S Y, Kirschner M W. Physical and chemical properties of purified tau factor and the role of tau in microtubule assembly. J. Mol. Biol. 1977; 116: 227-247.
8. Schweers O, Schonbrunn-Hanebeck E, Marx A, Mandelkow E. Structural studies of tau protein and Alzheimer paired helical filaments show no evidence for beta-structure. J. Biol. Chem. 1994; 269: 24290-24297.
9. Friedhoff P, Schneider A, Mandelkow E M, Mandelkow E. Rapid assembly of Alzheimer-like paired helical filaments from microtubule-associated protein tau monitored by fluorescence in solution. Biochemistry 1998; 37: 10223-10230.
10. Wang Y, Mandelkow E. Tau in physiology and pathology. Nat. Rev. Neurosci. 2016; 17: 5-21. Doi 10.1038/nrn.2015.1
11. Iqbal K, Liu F, Gong C X. Tau and neurodegenerative disease: the story so far. Nat. Rev. Neurol. 2016; 12: 15-27. Doi 10.1038/nrneurol.2015.225
12. Forman M S, Lee V M, Trojanowski J Q. New insights into genetic and molecular mechanisms of brain degeneration in tauopathies. J. Chem. Neuroanat 2000; 20: 225-244.
13. Lee V M-Y, Goedert M, Trojanoswki J Q. Neurodegenerative tauopathies. Annu. Rev. Neurosci. 2001; 24: 1121-1159.
14. Arriagada P V, Growdon J H, Hedley-Whyte E T, Hyman B T. Neurofibrillary tangles but not senile plaques parallel duration and severity of Alzheimer's disease. Neurology 1992; 42: 631-639.
15. Hutton M, Lendon C L, Rizzu P, Baker M, Froelich S, Houlden H, Pickering-Brown S, Chakraverty S, Isaacs A, Grover A et al. Association of missense and 5'-splice-site mutations in tau with the inherited dementia FTDP-17. Nature 1998; 393: 702-705.
16. Ghetti B, Oblak A L, Boeve B F, Johnson K A, Dickerson B C, Goedert M. Invited review: Frontotemporal dementia caused by microtubule-associated protein tau gene (MAPT) mutations: a chameleon for neuropathology and neuroimaging. Neuropathol. Appl. Neurobiol. 2015; 41: 24-46. Doi 10.1111/nan.12213
17. Hanger D P, Anderton B H, Noble W. Tau phosphorylation: the therapeutic challenge for neurodegenerative disease. Trends Mol. Med. 2009; 15: 112-119. Doi 10.1016/j.molmed.2009.01.003
18. Hanger D P, Betts J C, Loviny T L, Blackstock W P, Anderton B H. New phosphorylation sites identified in hyperphosphorylated tau (paired helical filament-tau) from Alzheimer's disease brain using nanoelectrospray mass spectrometry. J. Neurochem. 1998; 71: 2465-2476.
19. Hanger D P, Byers H L, Wray S, Leung K Y, Saxton M J, Seereeram A, Reynolds C H, Ward M A, Anderton B H. Novel phosphorylation sites in tau from Alzheimer brain support a role for casein kinase 1 in disease pathogenesis. J. Biol. Chem. 2007; 282: 23645-23654. Doi 10.1074/jbc.M703269200
20. Morishima-Kawashima M, Hasegawa M, Takio K, Suzuki M, Yoshida H, Titani K, Ihara Y. Proline-directed and non-proline-directed phosphorylation of PHF-tau. J. Biol. Chem. 1995; 270: 823-829.
21. Braak E, Braak H, Mandelkow E M. A sequence of cytoskeleton changes related to the formation of neurofibrillary tangles and neuropil threads. Acta Neuropathol. 1994; 87: 554-567.
22. Mondragon-Rodriguez S, Perry G, Luna-Munoz J, Acevedo-Aquino M C, Williams S. Phosphorylation of tau protein at sites Ser(396-404) is one of the earliest events in Alzheimer's disease and Down syndrome. Neuropathol. Appl. Neurobiol. 2014; 40: 121-135. Doi 10.1111/nan.12084
23. Braak H, Thal D R, Ghebremedhin E, Del Tredici K. Stages of the pathologic process in Alzheimer disease: age categories from 1 to 100 years. J. Neuropathol. Exp. Neurol. 2011; 70: 960-969. Doi 10.1097/NEN.0b013e318232a379
24. Gu J, Congdon E E, Sigurdsson E M. Two novel Tau antibodies targeting the 396/404 region are primarily taken up by neurons and reduce Tau protein pathology. J. Biol. Chem. 2013; 288: 33081-33095. Doi 10.1074/jbc.M113.494922
25. Ittner A, Bertz J, Suh L S, Stevens C H, Gotz J, Ittner L M. Tau-targeting passive immunization modulates aspects of pathology in tau transgenic mice. J. Neurochem. 2015; 132: 135-145. Doi 10.1111/jnc.12821
26. Walls K C, Ager R R, Vasilevko V, Cheng D, Medeiros R, LaFerla F M. p-Tau immunotherapy reduces soluble and insoluble tau in aged 3xTg-A D mice. Neurosci. Lett. 2014; 575: 96-100. Doi 10.1016/j.neulet.2014.05.047
27. Boutajangout A, Quartermain D, Sigurdsson E M. Immunotherapy targeting pathological tau prevents cognitive decline in a new tangle mouse model. J. Neurosci. 2010; 30: 16559-16566. Doi 10.1523/JNEUROSCI.4363-10.2010
28. Bi M, Ittner A, Ke Y D, Gotz J, Ittner L M. Tau-targeted immunization impedes progression of neurofibrillary histopathology in aged P301L tau transgenic mice. PloS One 2011; 6: e26860. Doi 10.1371/journal.pone.0026860
29. d'Abramo C, Acker C M, Jimenez H T, Davies P. Tau passive immunotherapy in mutant P301L mice: antibody affinity versus specificity. PloS One 2013; 8: e62402. Doi 10.1371/journal.pone.0062402
30. Asuni A A, Boutajangout A, Quartermain D, Sigurdsson E M. Immunotherapy targeting pathological tau conformers in a tangle mouse model reduces brain pathology with associated functional improvements. J. Neurosci. 2007; 27: 9115-9129. Doi 10.1523/JNEUROSCI.2361-07.2007
31. Boutajangout A, Ingadottir J, Davies P, Sigurdsson E M. Passive immunization targeting pathological phospho-tau protein in a mouse model reduces functional decline and clears tau aggregates from the brain. J. Neurochem. 2011; 118: 658-667. Doi 10.1111/j.1471-4159.2011.07337.x
32. Dawson H N, Ferreira A, Eyster M V, Ghoshal N, Binder L I, Vitek M P. Inhibition of neuronal maturation in primary hippocampal neurons from tau deficient mice. J. Cell Sci. 2001; 114: 1179-1187.
33. Yoshiyama Y, Higuchi M, Zhang B, Huang S M, Iwata N, Saido T C, Maeda J, Suhara T, Trojanowski J Q, Lee V M. Synapse loss and microglial activation precede tangles in a P301S tauopathy mouse model. Neuron 2007; 53: 337-351.
34. Lewis J, McGowan E, Rockwood J, Melrose H, Nacharaju P, Van Slegtenhorst M, Gwinn-Hardy K, Paul M M, Baker M, Yu X et al. Neurofibrillary tangles, amyotrophy and progressive motor disturbance in mice expressing mutant (P301L) tau protein. Nat. Genet. 2000; 25: 402-405.
35. Goedert M, Jakes R, Vanmechelen E. Monoclonal antibody AT8 recognises tau protein phosphorylated at both serine 202 and threonine 205. Neurosci. Lett. 1995; 189: 167-169.
36. Malia T J, Teplyakov A, Ernst R, Wu S J, Lacy E R, Liu X, Vandermeeren M, Mercken M, Luo J, Sweet R W et al. Epitope mapping and structural basis for the recognition of phosphorylated tau by the anti-tau antibody AT8. Proteins 2016; 84: 427-434. Doi 10.1002/prot.24988
37. Porzig R, Singer D, Hoffmann R. Epitope mapping of mAbs AT8 and Tau5 directed against hyperphosphorylated regions of the human tau protein. Biochem. Biophy. Res. Commun. 2007; 358: 644-649. Doi 10.1016/j.bbrc.2007.04.187
38. Otvos L, Jr., Feiner L, Lang E, Szendrei G I, Goedert M, Lee V M-Y. Monoclonal antibody PHF-1 recognizes tau protein phosphorylated at serine residues 396 and 404. J. Neurosci. Res. 1994; 39: 669-673.
39. Hong M, Zhukareva V, Vogelsberg-Ragaglia V, Wszolek Z, Reed L, Miller B I, Geschwind D H, Bird T D, McKeel D, Goate A et al. Mutation-specific functional impairments in distinct tau isoforms of hereditary FTDP-17. Science 1998; 282: 1914-1917.
40. Giasson B I, Forman M S, Golbe L I, Graves C L, Kotzbauer P T, Trojanoswki J Q, Lee V M-Y. Initiation and synergistic fibrillization of tau and alpha-synuclein. Science 2003; 300: 636-640.
41. Petry F R, Pelletier J, Bretteville A, Morin F, Calon F, Hebert S S, Whittington R A, Planel E. Specificity of anti-tau antibodies when analyzing mice models of Alzheimer's disease: problems and solutions. PloS One 2014; 9: e94251. Doi 10.1371/journal.pone.0094251
42. McMillan P, Korvatska E, Poorkaj P, Evstafjeva Z, Robinson L, Greenup L, Leverenz J, Schellenberg G D, D'Souza I. Tau isoform regulation is region- and cell-specific in mouse brain. J. Comp. Neurol. 2008; 511: 788-803. Doi 10.1002/cne.21867
43. Guo J L, Lee V M. Cell-to-cell transmission of pathogenic proteins in neurodegenerative diseases. Nat. Med. 2014; 20: 130-138. Doi 10.1038/nm.3457
44. Lewis J, Dickson D W. Propagation of tau pathology: hypotheses, discoveries, and yet unresolved questions from experimental and human brain studies. Acta Neuropathol. 2016; 131: 27-48. Doi 10.1007/s00401-015-1507-z
45. Mohamed N V, Herrou T, Plouffe V, Piperno N, Leclerc N. Spreading of tau pathology in Alzheimer's disease by cell-to-cell transmission. Eur. J. Neurosci. 2013; 37: 1939-1948. Doi 10.1111/ejn.12229
46. Boimel M, Grigoriadis N, Lourbopoulos A, Haber E, Abramsky O, Rosenmann H. Efficacy and safety of immunization with phosphorylated tau against neurofibrillary tangles in mice. Exp. Neurol. 2010; 224: 472-485. Doi 10.1016/j.expneurol.2010.05.010
47. Troquier L, Caillierez R, Burnouf S, Fernandez-Gomez F J, Grosjean M E, Zommer N, Sergeant N, Schraen-Maschke S, Blum D, Buee L. Targeting phospho-Ser422 by active Tau Immunotherapy in the THYTau22 mouse model: a suitable therapeutic approach. Curr. Alzheimer Res. 2012; 9: 397-405.
48. Yanamandra K, Kfoury N, Jiang H, Mahan T E, Ma S, Maloney S E, Wozniak D F, Diamond M I, Holtzman D M. Anti-tau antibodies that block tau aggregate seeding in vitro markedly decrease pathology and improve cognition in vivo. Neuron 2013; 80: 402-414. Doi 10.1016/j.neuron.2013.07.046
49. Collin L, Bohrmann B, Gopfert U, Oroszlan-Szovik K, Ozmen L, Gruninger F. Neuronal uptake of tau/pS422 antibody and reduced progression of tau pathology in a mouse model of Alzheimer's disease. Brain 2014; 137: 2834-2846. Doi 10.1093/brain/awu213

A number of embodiments of the disclosure have been described. Nevertheless, it will be understood that various modifications may be made without departing from the spirit and scope of the disclosure. Accordingly, other embodiments are within the scope of the following claims.

Unless defined otherwise, all technical and scientific terms used herein have the same meanings as commonly understood by one of skill in the art to which the disclosed disclosure belongs. Publications cited herein and the materials for which they are cited are specifically incorporated by reference.

Those skilled in the art will recognize, or be able to ascertain using no more than routine experimentation, many equivalents to the specific embodiments of the disclosure described herein. Such equivalents are intended to be encompassed by the following claims.

What is claimed is:

1. An antibody or antigen binding fragment thereof comprising a light chain and a heavy chain, wherein the light chain comprises CDR1, CDR2, and CDR3 of SEQ ID NO: 7, 8, and 9, respectively, and the heavy chain comprises CDR1, CDR2, and CDR3 of SEQ ID NO: 10, 11, and 12, respectively.

2. The antibody according to claim 1, comprising the light chain having the sequence of SEQ ID NO: 5 and the heavy chain having the sequence of SEQ ID NO: 6.

3. The antibody or antigen binding fragment thereof according to claim 1, wherein the light chain has the amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO: 5 and/or the heavy chain has the amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO: 6.

4. The antibody or the antigen binding fragment thereof according to claim 1, wherein the antibody is a murine monoclonal antibody, a humanized antibody, a chimeric antibody, an intrabody (Fab) fragment a single chain fragment variable (scFv) antibody, or a fragment antigen-binding (Fab fragment).

5. A kit comprising an antibody or antigen binding fragment thereof according to claim 1, the kit comprising reagents required for processing of a sample for an immunoassay, reagents for conducting the immunoassay, and instructional materials for performing the immunoassay.

6. A method of detecting tau protein in a subject, comprising administering to the subject an antibody or antigen binding fragment thereof according to claim 1, and detecting and/or quantifying the antibody or antigen binding fragment thereof bound to tau protein in the subject.

7. An antibody or an antigen binding fragment thereof according to claim 1 that is conjugated to an enzyme, radioisotope, fluorescent, or a bioluminescent label.

8. The antibody or the antigen binding fragment thereof according to claim 7, wherein the enzyme label is horseradish peroxidase, alkaline phosphatase, β-galactosidase, luciferase, acetylcholine esterase, or glucose oxidase.

9. The antibody or the antigen binding fragment thereof according to claim 7, wherein the radioisotope label is $^{125}$I, $^{35}$S, $^{14}$C, $^{32}$P and $^{3}$H.

10. The antibody or the antigen binding fragment thereof according to claim 7, wherein the fluorescent label is umbelliferone, fluorescein, rhodamine, dichlorotriazinylamine fluorescein, dansyl chloride, fluorescein isothiocyante (FITC), phycoerythrin (PE), Cy5-phycoerythrin (Cy5-PE), Cy7-phycoerythrin (Cy7-PE), allophycocyanin (APC), Cy7-allophycocyanin (Cy7-APC), texas red (TR) and cascade blue.

11. The antibody or the antigen binding fragment thereof according to claim 7, wherein the bioluminescent label is photoprotein aequorin, adenosine triphosphate, nicotinamide adenine dinucleotide and D-luciferin.

12. An antibody or antigen binding fragment thereof comprising a light chain and a heavy chain, wherein the light chain comprises CDR1, CDR2, and CDR3 of SEQ ID NO: 15, 16, and 17, respectively, and the heavy chain comprises CDR1, CDR2, and CDR3 of SEQ ID NO: 18, 19, and 20, respectively.

13. The antibody of claim 12, comprising the light chain having the sequence of SEQ ID NO: 13 and the heavy chain having the sequence of SEQ ID NO: 14.

14. The antibody or antigen binding fragment thereof according to claim 12, wherein the light chain has the amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO: 13 and/or the heavy chain has the amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO: 14.

15. An antibody or antigen binding fragment thereof comprising a light chain and a heavy chain, wherein the light chain comprises CDR1, CDR2, and CDR3 of SEQ ID NO: 23, 24, and 25, respectively, and the heavy chain comprises CDR1, CDR2, and CDR3 of SEQ ID NO: 26, 27, and 28, respectively.

16. An antibody or antigen binding fragment thereof comprising a light chain and a heavy chain, wherein the light chain comprises CDR1, CDR2, and CDR3 of SEQ ID NO: 31, 32, and 33, respectively, and the heavy chain comprises CDR1, CDR2, and CDR3 of SEQ ID NO: 34, 35, and 36, respectively; wherein the light chain comprises CDR1, CDR2, and CDR3 of SEQ ID NO: 39, 40, and 41, respectively, and the heavy chain comprises CDR1, CDR2, and CDR3 of SEQ ID NO: 42, 43, and 44, respectively; wherein the light chain comprises CDR1, CDR2, and CDR3 of SEQ ID NO: 47, 48, and 49, respectively, and the heavy chain comprises CDR1, CDR2, and CDR3 of SEQ ID NO: 50, 51, and 52, respectively.

* * * * *

SEQUENCE LISTING

```
<160> NUMBER OF SEQ ID NOS: 60

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
```

```
305                 310                 315                 320
Lys Cys Gly Ser Leu Gly Asn Ile His His Lys Pro Gly Gly Gln
            325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Asn
            355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
            405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
            435                 440

<210> SEQ ID NO 2
<211> LENGTH: 352
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Ala Glu Glu Ala
        35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
        115                 120                 125
Glu Pro Pro Lys Ser Gly Asp Arg Ser Gly Tyr Ser Ser Pro Gly Ser
    130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
        195                 200                 205
Lys His Gln Pro Gly Gly Gly Lys Val Gln Ile Val Tyr Lys Pro Val
    210                 215                 220
Asp Leu Ser Lys Val Thr Ser Lys Cys Gly Ser Leu Gly Asn Ile His
225                 230                 235                 240
```

```
His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 3

Glu Ile Val Tyr Lys Ser Pro Val Val Ser Gly Asp Thr Ser Pro Arg
1               5                   10                  15

His Leu Ser Cys
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 4

Asp Arg Ser Gly Tyr Ser Ser Pro Gly Ser Pro Gly Thr Pro Gly Ser
1               5                   10                  15

Arg Ser Arg Cys
            20

<210> SEQ ID NO 5
<211> LENGTH: 139
<212> TYPE: PRT
<213> ORGANISM: Mus musculus
```

<400> SEQUENCE: 5

Asp Ile Val Met Ser Gln Ser Pro Ser Leu Ala Val Ser Ala Gly
1               5                   10                  15

Glu Lys Val Thr Met Ser Cys Lys Ser Ser Gln Ser Leu Leu Tyr Ser
            20                  25                  30

Arg Asn Gln Lys Asn Tyr Leu Ala Trp Tyr Gln Gln Arg Pro Gly Gln
        35                  40                  45

Ser Pro Lys Leu Leu Ile Tyr Trp Ala Ser Ser Arg Glu Ser Gly Val
    50                  55                  60

Ser Asp Arg Phe Thr Gly Ser Gly Ser Gly Thr Asp Phe Thr Leu Thr
65                  70                  75                  80

Ile Ser Ser Val Lys Ala Asp Asp Leu Ala Val Tyr Tyr Cys Gln Gln
                85                  90                  95

Tyr Tyr Lys Ser Pro Leu Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val
    130                 135

<210> SEQ ID NO 6
<211> LENGTH: 134
<212> TYPE: PRT
<213> ORGANISM: Mus musculus

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Ser Met Asn Trp Val Arg Gln Pro Pro Gly Lys Ala Leu Glu Trp Leu
        35                  40                  45

Gly Cys Val Arg Asp Arg Ala Glu Gly Tyr Thr Thr Glu Tyr Ser Ala
    50                  55                  60

Ser Val Gln Gly Arg Phe Thr Ile Ser Arg Asp Asn Ser Gln Ser Ile
65                  70                  75                  80

Leu Tyr Leu Gln Met Asn Thr Leu Arg Pro Glu Asp Ser Ala Thr Tyr
                85                  90                  95

Tyr Cys Ala Arg Glu Arg Ala Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala
    130

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Lys Ser Ser Gln Ser Leu Leu Tyr Ser Arg Asn Gln Lys Asn Tyr Leu
1               5                   10                  15

Ala

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Tyr Trp Ala Ser Ser Arg Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Gln Gln Tyr Tyr Lys Ser Pro Leu Thr
1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Ala Thr Ser Gly Phe Thr Phe Thr Asp Phe Ser Met Asn
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Cys Val Arg Asp Arg Ala Glu Gly Tyr Thr Thr Glu
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Ala Arg Glu Arg Ala Phe Ala
1               5

<210> SEQ ID NO 13
<211> LENGTH: 140
<212> TYPE: PRT
<213> ORGANISM: Mus musculus

<400> SEQUENCE: 13

Glu Ile Val Leu Thr Gln Ser Ile Pro Ser Leu Thr Val Ser Ala Gly
1               5                   10                  15

Glu Arg Val Thr Ile Asn Cys Lys Ser Asn Gln Asn Leu Leu Trp Ser
            20                  25                  30

```
Gly Asn Gln Arg Tyr Cys Leu Val Trp His Gln Trp Lys Pro Gly Gln
                35                  40                  45

Thr Pro Thr Pro Leu Ile Thr Trp Thr Ser Asp Arg Tyr Ser Gly Val
 50                  55                  60

Pro Asp Arg Phe Ile Gly Gly Ser Val Thr Asp Phe Thr Leu Thr
 65                  70                  75                  80

Ile Ser Ser Val Gln Ala Glu Asp Val Ala Leu Tyr Phe Cys Gln His
                 85                  90                  95

His Leu His Ile Pro Pro Trp Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Ser Glu Gln Leu Thr Ser Gly Gly Ala Ser Val Val
    130                 135                 140

<210> SEQ ID NO 14
<211> LENGTH: 137
<212> TYPE: PRT
<213> ORGANISM: Mus musculus

<400> SEQUENCE: 14

Gln Val Gln Leu Gln Gln Ser Gly Ala Glu Leu Val Gln Pro Gly Gly
 1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Thr Gly Leu Glu Trp Val
            35                  40                  45

Ala Glu Ile Arg Leu Lys Ser Tyr Asn Tyr Ala Thr His Tyr Ala Glu
        50                  55                  60

Ser Val Thr Gly Arg Phe Thr Ile Ser Arg Asp Asp Ser Lys Asn Arg
 65                  70                  75                  80

Val Tyr Leu Gln Met Asn Asn Leu Gly Pro Asp Asp Thr Gly Ile Tyr
                 85                  90                  95

Tyr Cys Thr Thr Gly Gly Ala Tyr His Pro Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala
    130                 135

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Lys Ser Asn Gln Asn Leu Leu Trp Ser Gly Asn Gln Arg Tyr Cys Leu
 1               5                  10                  15

Val

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 16

Thr Trp Thr Ser Asp Arg Tyr Ser
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gln His His Leu His Ile Pro Pro Trp Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Val Ala Ser Gly Phe Thr Phe Ser Asn Tyr Trp Met Asn
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19

Glu Ile Arg Leu Lys Ser Tyr Asn Tyr Ala Thr His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Thr Thr Gly Gly Ala Tyr His Pro Phe Asp Tyr
1               5                   10

<210> SEQ ID NO 21
<211> LENGTH: 107
<212> TYPE: PRT
<213> ORGANISM: Mus musculus

<400> SEQUENCE: 21

Asp Ile Leu Leu Thr Gln Ser Pro Ala Ile Leu Ser Val Ser Pro Gly
1               5                   10                  15

Glu Arg Asp Ser Phe Ser Cys Arg Ala Ser Gln Asn Ile Gly Thr Ser
                20                  25                  30

Ile His Trp Tyr Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Val Asn Ser Val Glu Ser
65                  70                  75                  80
```

```
Glu Asp Val Ala Asp Tyr Tyr Cys Gln Gln Thr Lys Thr Trp Pro Thr
                85                  90                  95

Thr Phe Gly Ala Gly Thr Lys Leu Asp Leu Lys
            100                 105
```

<210> SEQ ID NO 22
<211> LENGTH: 120
<212> TYPE: PRT
<213> ORGANISM: Mus musculus

<400> SEQUENCE: 22

```
Glu Val Gln Leu Val Glu Ser Gly Gly Ser Val Lys Pro Gly Gly
1               5                   10                  15

Ser Leu Lys Leu Ser Cys Ala Ala Ser Gly Phe Thr Phe Ser Ser Tyr
                20                  25                  30

Ala Leu Ser Trp Val Arg Gln Thr Pro Glu Lys Arg Leu Glu Trp Val
            35                  40                  45

Ala Ser Ile Thr Ser Gly Gly Ser Tyr Thr Tyr Phe Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Thr Arg Pro Gly Asn Tyr Asp Gly Ala Trp Cys Ala Tyr Trp Gly Gln
            100                 105                 110

Gly Thr Leu Val Thr Val Ser Ser
        115                 120
```

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

```
Gln Asn Ile Gly Thr Ser
1               5
```

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 24

```
Tyr Ala Ser Xaa
1
```

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

-continued

Gln Gln Thr Lys Thr Trp Pro Thr Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

Gly Phe Thr Phe Ser Ser Tyr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Ile Thr Ser Gly Gly Ser Tyr Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Thr Arg Pro Gly Asn
1               5

<210> SEQ ID NO 29
<211> LENGTH: 139
<212> TYPE: PRT
<213> ORGANISM: Mus musculus

<400> SEQUENCE: 29

Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Arg
                20                  25                  30

Asn Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Tyr Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val
    130                 135

<210> SEQ ID NO 30

```
<211> LENGTH: 137
<212> TYPE: PRT
<213> ORGANISM: Mus musculus

<400> SEQUENCE: 30

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Thr Gly Leu Glu Trp Val
            35                  40                  45

Ala Glu Ile Arg Leu Lys Ser Tyr Asn Tyr Ala Thr His Tyr Ala Glu
        50                  55                  60

Ser Val Thr Gly Arg Phe Thr Ile Ser Arg Asp Asp Ser Lys Asn Arg
65                  70                  75                  80

Val Tyr Leu Gln Met Asn Asn Leu Gly Pro Asp Asp Thr Gly Ile Tyr
                85                  90                  95

Tyr Cys Thr Thr Gly Gly Ala Tyr His Pro Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala
    130                 135

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Gln Ser Leu Leu Tyr Arg Asn Asn Gln Lys Asn Tyr
 1               5                  10

<210> SEQ ID NO 32
<211> LENGTH: 4
<212> TYPE: PRT
<213> ORGANISM: Artificial Sequence
<220> FEATURE:
<223> OTHER INFORMATION: Synthetic Construct

<400> SEQUENCE: 32

Trp Ala Ser Thr
 1

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Gln Tyr Tyr Thr Tyr Pro Tyr Thr
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 34

Gly Phe Thr Phe Ser Asn Tyr Trp
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Ile Arg Leu Lys Ser Tyr Asn Tyr Ala Thr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Thr Gly Gly Ala Tyr
1               5

<210> SEQ ID NO 37
<211> LENGTH: 139
<212> TYPE: PRT
<213> ORGANISM: Mus musculus

<400> SEQUENCE: 37

Asp Ile Val Met Ser Gln Ser Pro Ser Ser Leu Ala Val Ser Val Gly
1               5                   10                  15

Glu Lys Val Thr Leu Thr Cys Lys Ser Ser Arg Ser Leu Leu Tyr Arg
            20                  25                  30

Gly Asn Gln Glu Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Lys Ala Glu Asp Leu Ala Val Tyr Tyr Cys Gln Gln
                85                  90                  95

Tyr Tyr Thr Tyr Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val
    130                 135

<210> SEQ ID NO 38
<211> LENGTH: 139
<212> TYPE: PRT
<213> ORGANISM: Mus musculus

<400> SEQUENCE: 38

Glu Val Asn Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
```

-continued

```
                20                  25                  30
Trp Met Asn Trp Val Arg Gln Ser Pro Glu Lys Gly Leu Glu Trp Val
         35                  40                  45
Ala Glu Ile Arg Leu Lys Ser Asp Asn Phe Ala Thr His Tyr Ala Glu
 50                  55                  60
Ser Val Lys Gly Arg Phe Thr Ile Ser Arg Asp Asp Ser Lys Ser Ser
 65                  70                  75                  80
Val Tyr Leu Gln Thr Asn Asn Leu Arg Ala Glu Asp Thr Gly Ile Tyr
                 85                  90                  95
Tyr Cys Thr Leu Met Arg Gly Asp Tyr Gly Ala Glu Phe Ala Tyr Trp
            100                 105                 110
Gly Gln Gly Thr Leu Ala Ile Val Ser Ala Ala Lys Thr Thr Pro Pro
        115                 120                 125
Ser Val Tyr Pro Leu Ala Pro Gly Ser Ala Ala
    130                 135

<210> SEQ ID NO 39
<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Arg Ser Leu Leu Tyr Arg Gly Asn Gln Glu Asn Phe
 1               5                  10

<210> SEQ ID NO 40
<211> LENGTH: 4
<212> TYPE: PRT
<213> ORGANISM: Artificial Sequence
<220> FEATURE:
<223> OTHER INFORMATION: Synthetic Construct

<400> SEQUENCE: 40

Trp Ala Ser Thr
 1

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Gln Tyr Tyr Thr Tyr Pro Tyr Thr
 1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Gly Phe Thr Phe Ser Asp Tyr Trp
 1               5

<210> SEQ ID NO 43
<211> LENGTH: 11
<212> TYPE: PRT
```

```
<213> ORGANISM: Artificial Sequence
<220> FEATURE:
<223> OTHER INFORMATION: Synthetic Construct

<400> SEQUENCE: 43

Ile Arg Leu Lys Ser Asp Asn Phe Ala Thr His
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Leu Met Arg Gly Asp
1               5

<210> SEQ ID NO 45
<211> LENGTH: 148
<212> TYPE: PRT
<213> ORGANISM: Mus musculus

<400> SEQUENCE: 45

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Gly Ala Tyr Thr
            100                 105                 110

Phe Gly Gly Gly Thr Lys Leu Glu Ile Lys Arg Ala Asp Ala Ala Pro
        115                 120                 125

Thr Val Ser Ile Phe Pro Pro Ser Ser Glu Gln Leu Thr Ser Gly Gly
    130                 135                 140

Ala Ser Val Val
145

<210> SEQ ID NO 46
<211> LENGTH: 134
<212> TYPE: PRT
<213> ORGANISM: Mus musculus

<400> SEQUENCE: 46

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Ser Met Asn Trp Asp Arg Gln Pro Pro Gly Lys Ala Leu Glu Trp Leu
        35                  40                  45

Gly Cys Val Arg Asp Arg Ala Glu Gly Tyr Thr Thr Glu Tyr Ser Ala
    50                  55                  60
```

Ser Val Gln Gly Arg Phe Thr Ile Ser Arg Asp Asn Ser Gln Ser Ile
65                  70                  75                  80

Leu Tyr Leu Gln Met Asn Thr Leu Arg Pro Glu Asp Ser Ala Thr Tyr
                85                  90                  95

Tyr Cys Ala Arg Glu Arg Ala Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala
    130

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Lys Ser Val Ser Thr Ser Gly Tyr Ser Tyr
1               5                   10

<210> SEQ ID NO 48
<211> LENGTH: 4
<212> TYPE: PRT
<213> ORGANISM: Artificial Sequence
<220> FEATURE:
<223> OTHER INFORMATION: Synthetic Construct

<400> SEQUENCE: 48

Leu Ala Ser Asn
1

<210> SEQ ID NO 49
<211> LENGTH: 19
<212> TYPE: PRT
<213> ORGANISM: Artificial Sequence
<220> FEATURE:
<223> OTHER INFORMATION: Synthetic Construct

<400> SEQUENCE: 49

His Ile Arg Glu Leu Thr Arg Ser Glu Gly Gly Pro Ser Trp Lys Gly
1               5                   10                  15

Ala Tyr Thr

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Gly Phe Thr Phe Thr Asp Phe Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Cys Val Arg Asp Arg Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Thr Tyr Tyr Cys Ala Arg Glu Arg Ala
1               5

<210> SEQ ID NO 53
<211> LENGTH: 108
<212> TYPE: PRT
<213> ORGANISM: Artificial Sequence
<220> FEATURE:
<223> OTHER INFORMATION: Synthetic Construct

<400> SEQUENCE: 53

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
                20                  25                  30

Ile His Trp Tyr Gln Gln Arg Thr Asn Gly Ser Pro Arg Leu Leu Ile
            35                  40                  45

Lys Tyr Thr Ser Glu Ser Ile Ser Gly Ile Pro Ser Arg Phe Gly Gly
50                  55                  60

Ser Gly Ser Gly Thr Asp Phe Thr Leu Ser Val Asn Gly Val Glu Ser
65                  70                  75                  80

Glu Asp Val Ala Asp Tyr Tyr Cys Gln Gln Thr Lys Thr Trp Pro Thr
                85                  90                  95

Thr Phe Gly Ala Gly Thr Lys Leu Glu Leu Lys Arg
            100                 105

<210> SEQ ID NO 54
<211> LENGTH: 121
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Ser Ile Thr Arg Gly Gly Ser Tyr Thr Tyr Phe Pro Asp Ser Val
50                  55                  60

Lys Gly Arg Phe Thr Ile Ser Arg Asp Asn Thr Lys Asp Thr Leu Tyr
65                  70                  75                  80

Leu Gln Met Ser Ser Leu Arg Ser Glu Asp Thr Ala Met Tyr Tyr Cys
                85                  90                  95

Thr Arg Gln Gly Asn Tyr Asp Gly Ala Trp Cys Asp Tyr Trp Gly Gln
            100                 105                 110

Gly Thr Leu Val Thr Val Ser Ala Ala
        115                 120

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Gln Asn Ile Gly Thr Ser
1               5

<210> SEQ ID NO 56
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 56

Tyr Thr Ser Xaa
1

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Thr Lys Thr Trp Pro Thr Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Gly Phe Thr Phe Ser Ser Tyr Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Ile Thr Arg Gly Gly Ser Tyr Thr
1               5

<210> SEQ ID NO 60
<211> LENGTH: 5

```
<212> TYPE: PRT
<213> ORGANISM: Artificial Sequence
<220> FEATURE:
<223> OTHER INFORMATION: Synthetic Construct

<400> SEQUENCE: 60

Thr Arg Gln Gly Asn
1               5
```